(12) United States Patent
Bornzin et al.

(10) Patent No.: US 8,750,981 B2
(45) Date of Patent: Jun. 10, 2014

(54) SYSTEMS AND METHODS FOR ASSESSING HEART FAILURE AND CONTROLLING CARDIAC RESYNCHRONIZATION THERAPY USING HYBRID IMPEDANCE MEASUREMENT CONFIGURATIONS

(75) Inventors: Gene A. Bornzin, Simi Valley, CA (US); Xiaoyi Min, Thousand Oaks, CA (US); Laurence S. Sloman, West Hollywood, CA (US); Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 131 days.

(21) Appl. No.: 13/217,554

(22) Filed: Aug. 25, 2011

(65) Prior Publication Data

US 2013/0053912 A1 Feb. 28, 2013

(51) Int. Cl.
| | | |
|---|---|---|
| *A61B 5/05* | (2006.01) | |
| *A61B 5/053* | (2006.01) | |
| *A61N 1/36* | (2006.01) | |
| *A61N 1/368* | (2006.01) | |
| *A61B 5/0205* | (2006.01) | |

(52) U.S. Cl.
CPC .............. *A61B 5/053* (2013.01); *A61B 5/0538* (2013.01); *A61N 1/36185* (2013.01); *A61N 1/3686* (2013.01); *A61B 5/0205* (2013.01)
USPC ............................................. 600/547; 607/28

(58) Field of Classification Search
USPC ................................ 607/17, 28; 600/508, 547
See application file for complete search history.

(56) References Cited

U.S. PATENT DOCUMENTS

| | | | |
|---|---|---|---|
| 6,269,264 B1 | 7/2001 | Weyant et al. | |
| 6,512,952 B2 | 1/2003 | Stahmann et al. | |
| 6,628,988 B2 | 9/2003 | Kramer et al. | |
| 6,643,546 B2 | 11/2003 | Mathis et al. | |
| 6,795,733 B1 * | 9/2004 | Lu .................................... | 607/17 |
| 7,010,347 B2 | 3/2006 | Schecter | |
| 7,248,925 B2 | 7/2007 | Bruhns et al. | |
| 7,272,436 B2 | 9/2007 | Gill et al. | |
| 7,272,443 B2 | 9/2007 | Min et al. | |
| 7,505,814 B2 | 3/2009 | Bornzin et al. | |
| 7,590,446 B1 | 9/2009 | Min et al. | |
| 7,676,264 B1 | 3/2010 | Pillai et al. | |
| 2006/0241512 A1 * | 10/2006 | Kwok et al. .................. | 600/547 |
| 2008/0249583 A1 | 10/2008 | Salo et al. | |
| 2009/0299423 A1 | 12/2009 | Min | |
| 2010/0121397 A1 | 5/2010 | Cholette | |
| 2010/0145405 A1 | 6/2010 | Min et al. | |
| 2011/0022110 A1 | 1/2011 | Min | |
| 2011/0022112 A1 | 1/2011 | Min | |
| 2011/0098772 A1 | 4/2011 | Min | |

FOREIGN PATENT DOCUMENTS

| | | |
|---|---|---|
| WO | 2010074611 A1 | 7/2010 |
| WO | 2010131998 A1 | 11/2010 |

* cited by examiner

*Primary Examiner* — Carl H Layno
*Assistant Examiner* — Jon Eric C Morales

(57) ABSTRACT

Techniques are provided for use with an implantable medical device for detecting and assessing heart failure and for controlling cardiac resynchronization therapy (CRT) based on impedance signals obtained using hybrid impedance configurations. The hybrid configurations exploit right atrial (RA)-based impedance measurement vectors and/or left ventricular (LV)-based impedance measurement vectors. In one example, current is injected between the device case and a ring electrode in the right ventricle (RV) or RA. RA-based impedance values are measured along vectors between the device case and an RA electrode. LV-based impedance values are measured along vectors between the device case and one or more electrodes of the LV. Heart failure and other cardiac conditions are detected and tracked using the measured impedance values. CRT delay parameters are also optimized based impedance. In this manner, multiple hybrid impedance measurement configurations are exploited whereby different vectors are used to inject current and measure impedance.

25 Claims, 12 Drawing Sheets

EXEMPLARY RA-BASED IMPEDANCE MEASUREMENT CONFIGURATIONS/TECHNIQUES

INJECT CURRENT BETWEEN:

(A) THE DEVICE CAN ELECTRODE OR THE SVC COIL ELECTRODE, AND (B) THE RV RING ELECTRODE, THE RV TIP ELECTRODE OR THE RV COIL ELECTRODE; OR

THE RA TIP ELECTRODE OR THE RA RING ELECTRODE AND THE DEVICE CAN — 200

MEASURE IMPEDANCE BETWEEN:

(A) THE RA RING ELECTRODE OR THE RA TIP ELECTRODE, AND (B) THE DEVICE CAN ELECTRODE OR THE SVC COIL ELECTRODE

OR BETWEEN THE SVC COIL ELECTRODE AND THE DEVICE CAN — 210

- DETECT, ESTIMATE OR ASSESS PARAMETERS REPRESENTATIVE OF HEART FAILURE OR OTHER HEART CONDITIONS FROM THE MEASURED IMPEDANCE VALUES

- OPTIMIZE OR ADJUST CRT DELAY PARAMETERS BASED ON THE MEASURED IMPEDANCE VALUES

- ISSUE WARNINGS WHEN APPROPRIATE

- RECORD DIAGNOSTICS — 218

*FIG. 3*

SYSTEMS AND METHODS FOR ASSESSING HEART FAILURE AND CONTROLLING CARDIAC RESYNCHRONIZATION THERAPY USING HYBRID IMPEDANCE MEASUREMENT CONFIGURATIONS

FIELD OF THE INVENTION

The invention generally relates to implantable cardiac rhythm management devices such as pacemakers, implantable cardioverter-defibrillators (ICDs) and cardiac resynchronization therapy (CRT) devices and, in particular, to techniques for measuring impedance using implantable devices equipped with multiple leads and further to techniques for optimizing CRT pacing delays based on impedance and for detecting and tracking heart failure.

BACKGROUND OF THE INVENTION

Heart failure is a debilitating disease in which abnormal function of the heart leads to inadequate blood flow to fulfill the needs of the tissues and organs of the body. Typically, the heart loses propulsive power because the cardiac muscle loses capacity to stretch and contract. Often, the ventricles do not adequately fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds cardiac muscle causing the ventricles to grow in volume in an attempt to pump more blood with each heartbeat, i.e. to increase the stroke volume. This places a still higher demand on the heart's oxygen supply. If the oxygen supply falls short of the growing demand, as it often does, further injury to the heart may result, typically in the form of myocardial ischemia or myocardial infarction. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

In view of the potential severity of heart failure, it is highly desirable to detect its onset within a patient and to track its progression so that appropriate therapy can be provided. Many patients suffering heart failure already have pacemakers or ICDs implanted therein or are candidates for such devices. Accordingly, it is desirable to provide such devices with the capability to automatically detect and track heart failure and various techniques exploiting electrical impedance signals measured by an implantable device have been developed. Techniques exploiting impedance are presented, for example, in U.S. Pat. No. 7,505,814 to Bornzin et al., entitled "System and Method for Evaluating Heart Failure based on Ventricular End-Diastolic Volume using an Implantable Medical Device" and in U.S. Pat. No. 7,272,443 to Min et al., entitled "System and Method for Predicting a Heart Condition based on Impedance Values using an Implantable Medical Device."

More recently, techniques for measuring impedance using hybrid impedance vectors were described in U.S. patent application Ser. No. 13/023,408, filed Feb. 8, 2011, of Min et al., entitled "Systems and Methods for Tracking Stroke Volume using Hybrid Impedance Configurations Employing a Multi-Pole Implantable Cardiac Lead", which is fully incorporated by reference herein. In one example described therein, current is injected between a large and stable reference electrode and a right ventricular (RV) ring electrode. The reference electrode may be, e.g., a coil electrode implanted within the superior vena cava (SVC) or the device case or "can" electrode. Impedance values are then measured along a set of different sensing vectors between the reference electrode and the electrodes of a multi-pole left ventricular (LV) lead implanted via the coronary sinus (CS). These techniques are generally referred to as hybrid techniques since different vectors are employed for injecting current than for measuring the resulting impedance/voltage. More specifically, the techniques may be referred to as "LV-based hybrid techniques" since LV electrodes are used to measure the impedance. The LV-based hybrid techniques advantageously allow impedance signals to be detected that exhibit significant variation throughout individual cardiac cycles to aid in the detection of stroke volume and related cardiac function parameters and to aid in the optimization of pacing delays for use with CRT.

It would be desirable to provide hybrid impedance measurement techniques that additionally or alternatively exploit electrodes of a right atrial (RA) lead for measuring impedance values (based on current injected via the RV.) It is to these ends that various aspects of the present invention are directed.

SUMMARY OF THE INVENTION

In an exemplary embodiment, a method is provided for use with an implantable medical device for implant within a patient having a lead system including an RV lead and an RA lead. Current is injected between a current injection reference electrode and an electrode in the RV, such as the RV ring or RV tip. The current injection reference electrode is preferably a relatively large and stable electrode (i.e., one that is relatively insensitive to patient motion artifacts and tissue property changes) such as the device can (or case) electrode or a coil electrode implanted within the SVC of the patient near the RA. Impedance values are then measured along a vector between a voltage sensing reference electrode and an electrode in or near the RA, such as an RA ring electrode. The voltage sensing reference electrode is also preferably a relatively large and stable electrode and can be the same reference electrode used for injecting current (e.g., the device can use the device case electrode both for injecting current in conjunction with an electrode in the RV and for then measuring impedance in conjunction with an electrode in or near the RA.) In this manner, a hybrid impedance detection configuration is exploited whereby an RV vector is used to inject current and an RA vector is used to measure impedance. At least one device function is then controlled based on the measured impedance values. The device function can comprise any function that can be performed or controlled by the device such as (a) detecting heart failure, interventricular dyssynchrony or other cardiac conditions based on the impedance values, (b) issuing warning signals in response to detection of such conditions, (c) optimizing atrioventricular (AV) and interventricular (VV) pacing delays for use with CRT based on the impedance values or (d) recording impedance-based diagnostic information.

In an illustrative example, the implantable device is a pacemaker, ICD or CRT device having an RA lead with a pair of tip and ring electrodes and an RV lead also having a pair of tip and ring electrodes. Both the RV and RA leads are implanted via the SVC. The RV lead also has an RV coil electrode positioned in the RV itself and a separate SVC coil electrode positioned in the SVC. Herein, the SVC coil is considered to be near the RA since the SVC is anatomically close to the RA. In the illustrative example, current is injected between either the device can electrode or the SVC electrode and at least one of the electrodes in the RV itself (i.e. the RV ring, RV tip or RV coil.) As such, the current injection vector exploits a relatively large and stable electrode, which generates a relatively wide electrical field for impedance measurement purposes. Note that the relatively wide field encompasses at least some non-cardiac thoracic fluids and tissues, as well as cardiac fluids and tissues, such that both intrathoracic and transthoracic (TTZ) impedance and intracardiac (ICZ) impedance are implicated. Insofar as the impedance measurement vector is concerned, in the illustrative example the device measures impedance between the RA tip or RA ring electrodes and the device can electrode (or the SVC coil electrode), thereby exploiting a different vector for impedance measurement as opposed to current injection. In other examples, instead of injecting current via the RV, current is injected RA ring to can or RA tip to can and then impedance is measured RA ring to can or RA tip to can.

Herein, configurations that exploit electrodes in or near the RA for use in measuring impedance are referred to as "RA-based impedance measurement configurations." The impedance values (Z) measured using the RA-based configurations are referred to herein as $Z_{RA}$ values to distinguish from other impedance values measured using other measurement configurations.

In at least some embodiments, the lead system also includes an LV lead implanted via the CS. In addition to measuring impedance ($Z_{RA}$) using the electrodes of the RA lead, the device also measures impedance ($Z_{LV}$) using electrodes of the LV lead. Herein, configurations that exploit electrodes on or near the LV for use in measuring impedance are referred to as "LV-based impedance measurement configurations." In an illustrative example, the LV lead is a quadpole LV lead implanted via the CS with a distal tip electrode (D1), a proximal ring electrode (P4), and a pair of intermediate ring electrodes (M2 and M3). For convenience, the LV electrodes are identified herein by the index "i" where i=1 refers to the D1 electrode, i=2 refers to the M2 electrode, i=3 refers to the M3 electrode and i=4 refers to the P4 electrode. Current is injected using any of the RV electrodes and either the SVC coil or the device can.

The RA-based and LV-based impedance measurements are then used to detect heart failure or other conditions, optimize AV and VV delays for use with CRT, or to perform or control any other suitable functions. In some examples, at least some of these functions are performed by or in conjunction with an external system—such as a device programmer—in communication with the implanted device.

In various examples described herein, impedance measurements are used but it should be understood that related electrical parameters might be detected and/or exploited instead such as admittance, conductance or immittance. Those skilled in the art can convert between these related parameters as needed. Herein, "values representative of impedance" is intended to include related electrical parameters such as admittance, conductance and immittance.

System and method implementations of the various exemplary embodiments are presented herein.

BRIEF DESCRIPTION OF THE DRAWINGS

Features and advantages of the described implementations can be more readily understood by reference to the following description taken in conjunction with the accompanying drawings.

FIG. 3 illustrates some exemplary RA-based impedance measurement techniques for use with the general RA-based technique of FIG. 2;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable Medical System

Figure 1:
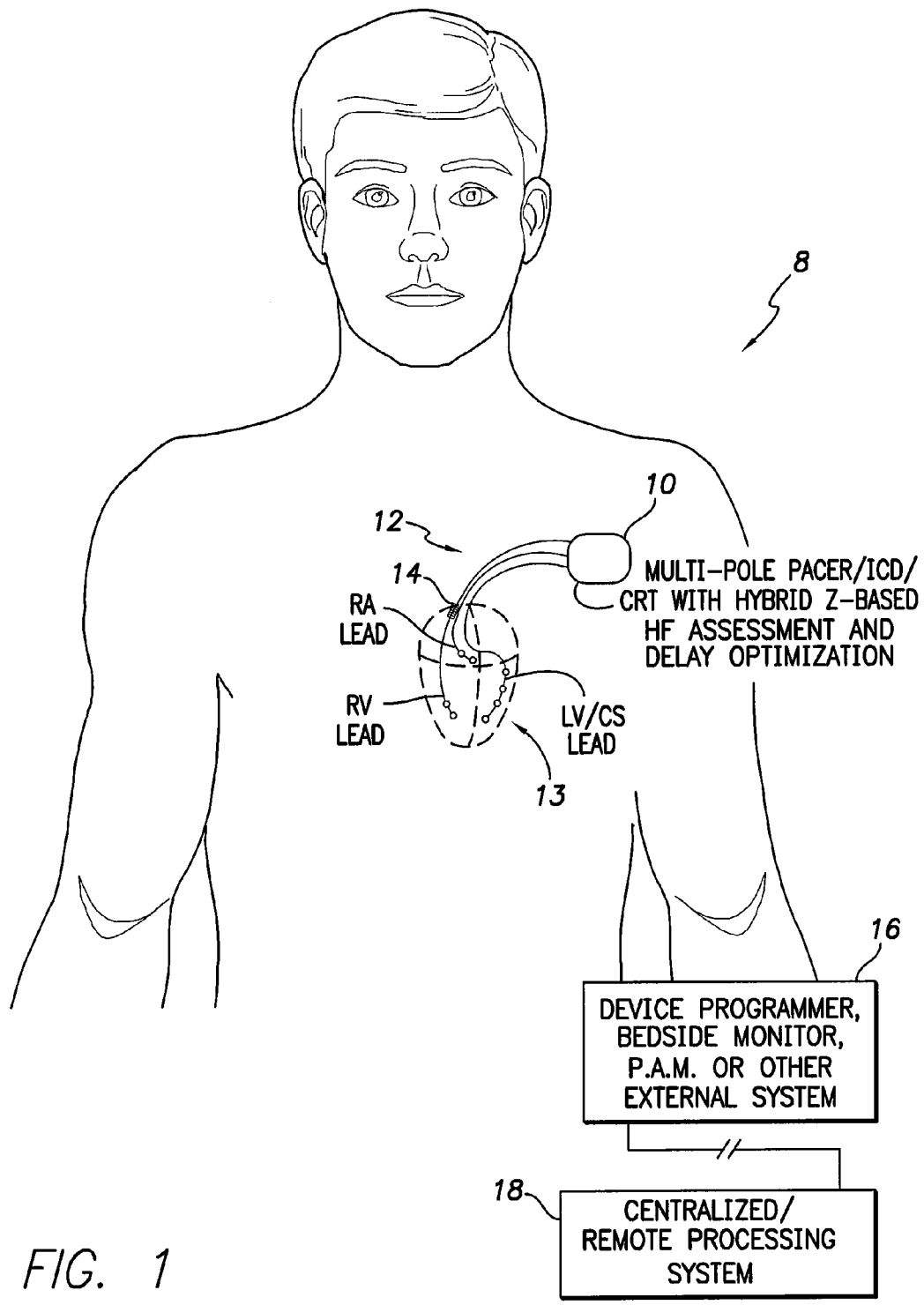
FIG. 1 illustrates pertinent components of an implantable medical system having a pacemaker, ICD or CRT device equipped to assess heart failure and optimize CRT delays based on impedance signals detected within a patient via various hybrid impedance measurement configurations.

FIG. 1 illustrates an implantable medical system 8 capable of assessing and tracking heart failure or related cardiac conditions based on impedance measured via various hybrid configurations and also capable of adjusting or optimizing AV and VV pacing delays for use with CRT. Implantable system 8 includes a pacer/ICD/CRT device 10 or other cardiac rhythm management device equipped with one or more leads 12 implanted on or within the heart of the patient, including a multi-pole LV lead implanted via the CS. To illustrate the multi-pole configuration of the LV lead, a set of electrodes 13 is shown distributed along the LV lead. In the examples described herein, a quad-pole (or "quadrapolar" or "quadripolar") lead is employed (such as the Quartet™ lead provided by St Jude Medical). Other suitable LV leads may instead be employed, including leads with more or fewer electrodes such as bipolar LV leads. Exemplary RV and RA leads are also shown that include tip/ring pairs. The RV lead includes an SVC coil 14, which can be used as a reference electrode for injecting current and, in some examples, can also be used as a reference electrode for measuring impedance. Other electrodes of various sizes and shapes may be additionally or alternatively provided, such as coil electrodes mounted in or on the LV, RV or the left atrium (LA.) See FIG. 10 for a more complete and accurate illustration of the location of various exemplary leads. Using the leads and their electrodes, various hybrid impedance measurement configurations are exploited, alone or in combination, including RA-based configurations wherein impedance is measured using an RA electrode and LV-based configurations wherein impedance is measured using an LV electrode.

Although identified as a pacer/ICD/CRT in FIG. 1, it should be understood that device 10 can be any suitably-equipped implantable medical device, such as a standalone pacemaker, ICD or CRT device, including CRT-D and CRT-P devices. In the following, for brevity, device 10 will be referred to simply as a pacer/ICD.

Based on impedance values measured using the hybrid configurations, the pacer/ICD can then optimize CRT pacing delays and/or detect and track heart failure or related conditions using techniques described below. Depending upon the particular conditions detected, the pacer/ICD will issue warning signals, if appropriate. For example, if heart failure is detected, warning signals may be generated to warn the patient or caregiver, either using an internal warning device (which can be part of the pacer/ICD) or using an external bedside monitor/handheld warning device 16 or other external system. The internal warning device may be a vibrating device or a "tickle" voltage device that, in either case, provides perceptible stimulation to the patient to alert the patient so that the patient may consult a physician. In one example, once the warning is felt, the patient positions an external warning device above his or her chest. The handheld device, which might be a personal advisory module (PAM), receives short-range telemetry signals from the implanted device and provides audible or visual verification of the warning signal. The handheld warning device thereby provides confirmation of the warning to the patient, who might otherwise be uncertain as to the reason for the internally generated warning signal. For further information regarding this warning/notification technique, see U.S. Pat. No. 7,272,436 to Gill et al.

If a bedside monitor is provided, the bedside monitor provides audible or visual alarm signals to alert the patient or caregivers, as well as providing textual or graphic displays. In addition, any diagnostic information pertaining to a deteriorating cardiac condition of the patient is transferred to the bedside monitor or is stored within the pacer/ICD for subsequent transmission to a device programmer for review by a clinician or other medical professional. The clinician may then prescribe therapies to address the condition. The clinician may also adjust the operation of the pacer/ICD to activate, deactivate or otherwise control any therapies that are automatically applied, including titration of medications if an implantable drug infusion pump is provided. The bedside monitor may be directly networked with an internet network site or a centralized processing system 18 for immediately notifying the clinician of any urgent medical condition. The centralized system may include such systems as Merlin.Net of St. Jude Medical, which may be used in conjunction with bedside monitors or similar devices such as the HouseCall™ remote monitoring system or the Merlin@home systems, also of St. Jude Medical.

In some implementations, the pacer/ICD itself detects heart failure and/or optimizes CRT delays based on impedance measurements made using its leads. In other implementations, the device transmits the measurements to the external systems 16 or 18, which perform the assessment. In the following examples, it is assumed that the pacer/ICD performs the functions using on-board components. An example where the external programmer performs the functions is described below with reference to FIG. 12.

Hence, FIG. 1 provides an overview of an implantable medical system for optimizing CRT pacing delays, detecting and tracking heart failure or other cardiac conditions, and delivering appropriate warning/notification signals and therapy where appropriate, etc. Embodiments may be implemented that do not necessarily perform all of these functions. For example, embodiments may be implemented that detect heart failure but do not automatically optimize CRT delays. Embodiments may be implemented that exploit RA-based impedance measurement configurations but not LV-based configurations. In addition, note that the particular locations of the implanted components shown in FIG. 1 are merely illustrative and may not necessarily correspond to actual implant locations.

RA-Based Impedance Measurement Hybrid Configurations

Figure 2:
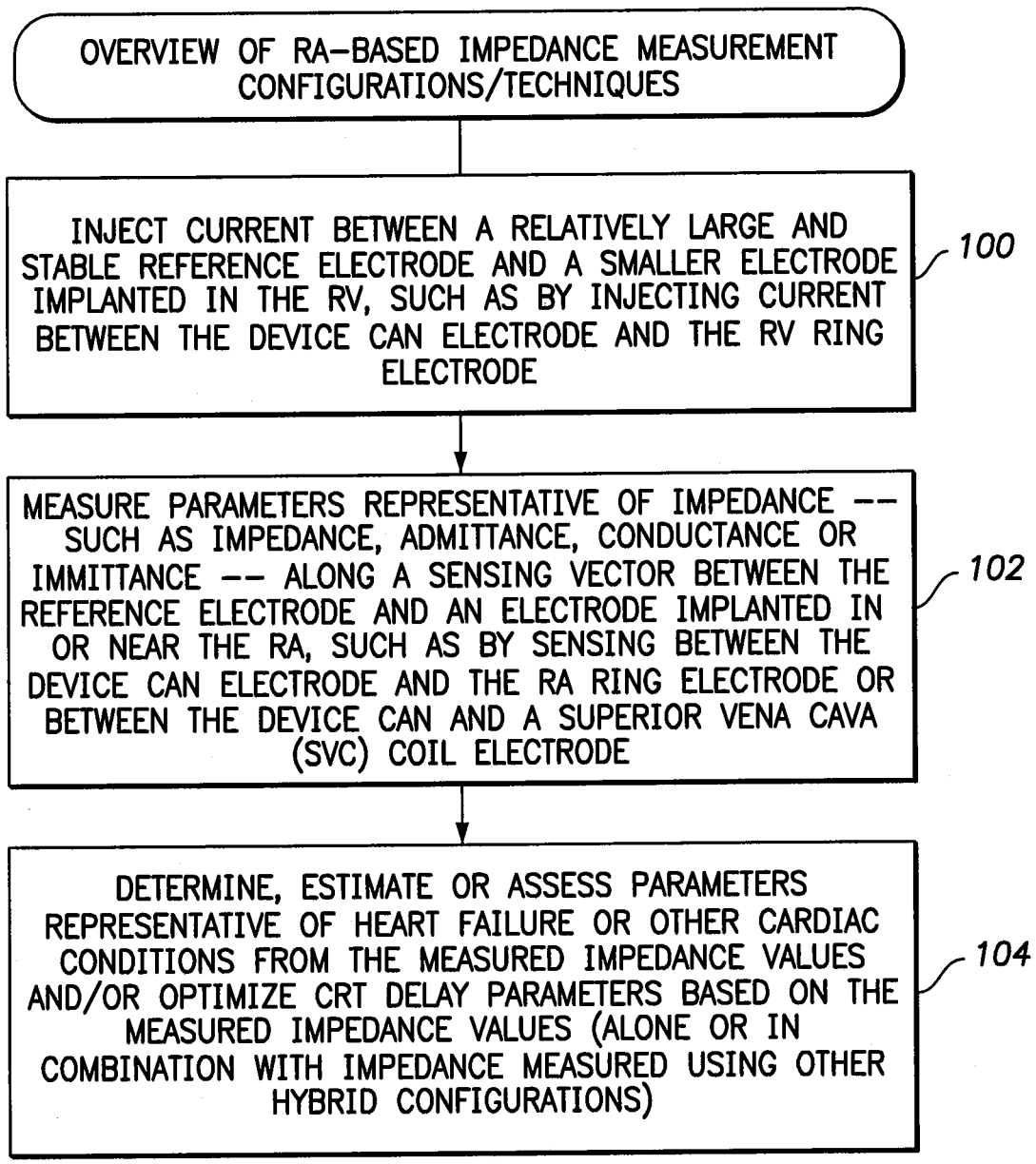
FIG. 2 provides an overview of RA-based hybrid techniques for assessing heart failure and optimizing CRT delays that may be performed by the system of FIG. 1 using RA-based impedance measurement configurations.

FIG. 2 broadly summarizes general techniques exploiting RA-based impedance measurement configurations that may be used by the components of the system of FIG. 1. Beginning at step 100, the pacer/ICD injects current between a relatively large and stable reference electrode and a smaller electrode of the RV lead, such as by injecting current between the device can (case) electrode and the RV ring. The use of the relatively large and stable device can electrode generates a relatively wide electrical field for impedance measurement purposes that is relatively insensitive to patient motion artifacts and/or changes in tissue properties. The relatively wide field encompasses at least some non-cardiac thoracic fluids and tissues, as well as cardiac fluids and tissues, such that both intrathoracic and intracardiac impedance is implicated. The device can is employed (in at least some examples) as the "reference" electrode due to its relatively large size and its stable location but other reference electrodes can instead be used so long as such electrodes are efficacious for the intended purposes described herein. For instance, in other examples, the SVC coil is used to instead inject current in conjunction with the RV electrode.

At step 102, the device then measures values representative of electrical impedance (such as impedance, admittance, conductance or immittance) along a sensing vector between the reference electrode and an electrode in or near the RA such as the RA tip, RA ring or SVC coil electrodes. As will be explained, this may be achieved by sensing voltage and then dividing the voltage by the magnitude of the injected current. In any case, current is injected using one vector and then impedance is measured using another vector, thereby providing for a hybrid impedance detection configuration. At step 104, the pacer/ICD then determines, estimates or assesses parameters representative of heart failure or other cardiac conditions from the measured impedance values ($Z_{RA}$) and/or optimizes CRT delay parameters (e.g. AV and VV delays) based on the measured impedance values (alone or in combination with impedance measured using other hybrid configurations such as the LV-based configurations discussed elsewhere herein.) Exemplary techniques are described below wherein $\Delta Z_{RA}$ values are exploited to optimize AV and VV delays or to detect and track heart failure.

Figure 4:
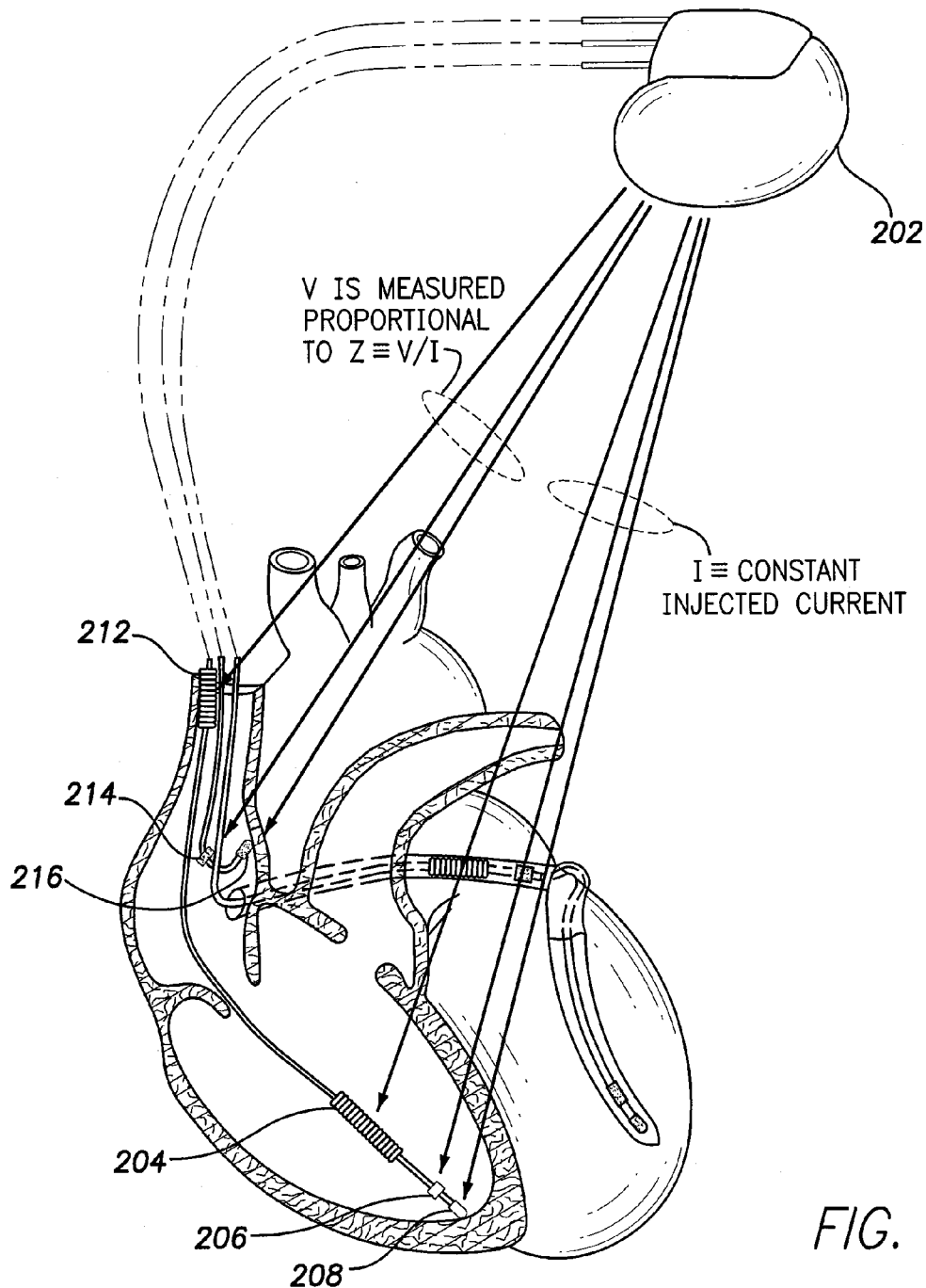
FIG. 4 illustrates vectors for use with the exemplary RA-based techniques of FIG. 3 along with an exemplary lead system.

FIG. 3 summarizes some particular RA-based configurations. At step 200, the pacer/ICD injects current between: (A) the device can electrode or the SVC coil electrode, and (B) the RV ring electrode, the RV tip electrode or the RV coil electrode. FIG. 4 illustrates these current injection vectors, specifically showing a device case (or can) electrode 202, an RV coil 204, an RV ring 206 and an RV tip 208, with the injection vectors shown therebetween. Alternatively, as shown in step 200 of FIG. 3, current may be injected between the RA tip electrode or RA ring electrode and the can. Insofar as the injection current is concerned, otherwise conventional techniques may be used for identifying preferred or optimal values for the magnitude of the injection current (which might depend upon the particular pair of electrodes used to inject the current.) An injection current corresponding to 50 volts (V) is appropriate in at least some examples is employed.

At step 210 of FIG. 3, the pacer/ICD measures impedance/voltage between: (A) the RA ring electrode or the RA tip electrode, and (B) the device can electrode or the SVC coil electrode. Alternatively, rather than using an electrode in the RA, an electrode near the RA may instead be used, particularly the SVC coil which is near the in-flow tract of the RA. That is, at step 210, impedance/voltage may alternatively be measured using the SVC coil electrode and the device can. FIG. 4 illustrates the various exemplary impedance measurement vectors between the device case (can) 202 and the SVC coil 212, RA ring 214 and RA tip 216, with the impedance/voltage measurement vectors shown therebetween (where the measured voltage is proportional to Z=V/I, with constant current (I)). Note that when current in injected between the RA tip electrode or the RA ring electrode and the can, the impedance is also preferably measured between the RA tip or RA ring and the can. Insofar as measuring impedance is concerned, otherwise conventional techniques may be employed to measure particular values representative of impedance. Impedance measurement techniques are discussed, for example, in U.S. Pat. No. 6,269,264 to Weyant et al., entitled "Method for Measuring Impedance in the Body." As noted, depending upon the particular implementation, any of various related electrical parameters can be sensed or measured, including impedance, admittance, conductance and immittance. Those skilled in the art can convert among the parameters, as needed. Note that other components of the system of FIG. 4 are discussed below, such as the LV electrodes shown therein.

At step 218 of FIG. 3, the pacer/ICD: detects, estimates or assesses parameters representative of heart failure or other heart conditions from the measured impedance values; optimizes or adjusts CRT delay parameters based on the measured RA-based impedance values; issues warnings when appropriate; and/or records diagnostics. Diagnostic information can include the impedance values determined by the device or parameters derived therefrom. This information may be recorded along with device operational data (such as the current pacing configuration, pacing rate, etc.) and patient physiological/anatomical data (such as current posture, heart rate, blood pressure, etc.), assuming such information is available. Warnings may be generated in response to detection of the onset or progression cardiac conditions made based on the impedance values or in response to significant changes in CRT delays triggered in response to changes in impedance. Particular techniques for detecting heart conditions and optimizing CRT delays are discussed below.

LV-Based Impedance Measurement Hybrid Configurations

Figure 5:
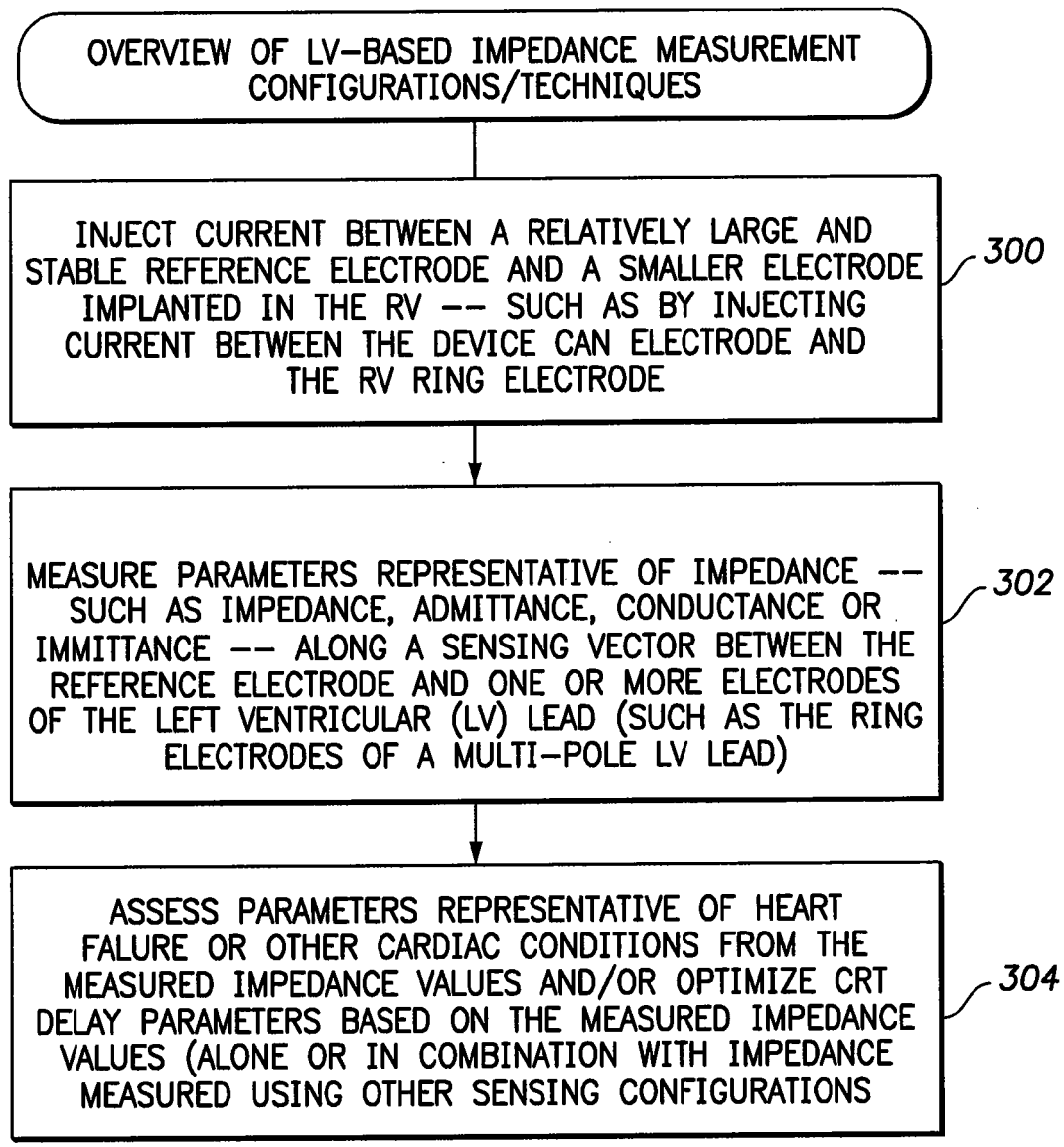
FIG. 5 provides an overview of LV-based hybrid techniques for assessing heart failure and optimizing CRT delays that may be performed by the system of FIG. 1 using LV-based impedance measurement configurations.

FIG. 5 broadly summarizes general techniques exploiting LV-based impedance measurement configurations that may be used by the components of the system of FIG. 1. At least some of these techniques are also discussed in the application of Min cited above. Beginning at step 300, the pacer/ICD injects current between a relatively large and stable reference electrode and a smaller electrode of the RV lead, such as by injecting current between the device can (or case) electrode and the RV ring as already discussed. At step 302, the device then measures values ($Z_{LV}$) representative of electrical impedance (such as impedance, admittance, conductance or immittance) along a sensing vector between the reference electrode and an electrode on or near the LV such as LV tip or LV ring electrodes, thereby providing another hybrid impedance detection configuration. At step 304, the pacer/ICD then determines, estimates or assesses parameters representative of heart failure or other cardiac conditions from the measured impedance values and/or optimizes CRT delay parameters (e.g. AV and VV delays) based on the measured impedance values (alone or in combination with impedance measured using other hybrid configurations such as the RA-based configurations discussed elsewhere herein.) Exemplary techniques are described below wherein $\Delta Z_{LV}$ values are exploited along with $\Delta Z_{RA}$ values to optimize AV and VV delays or to detect and track heart failure.

Figure 6:
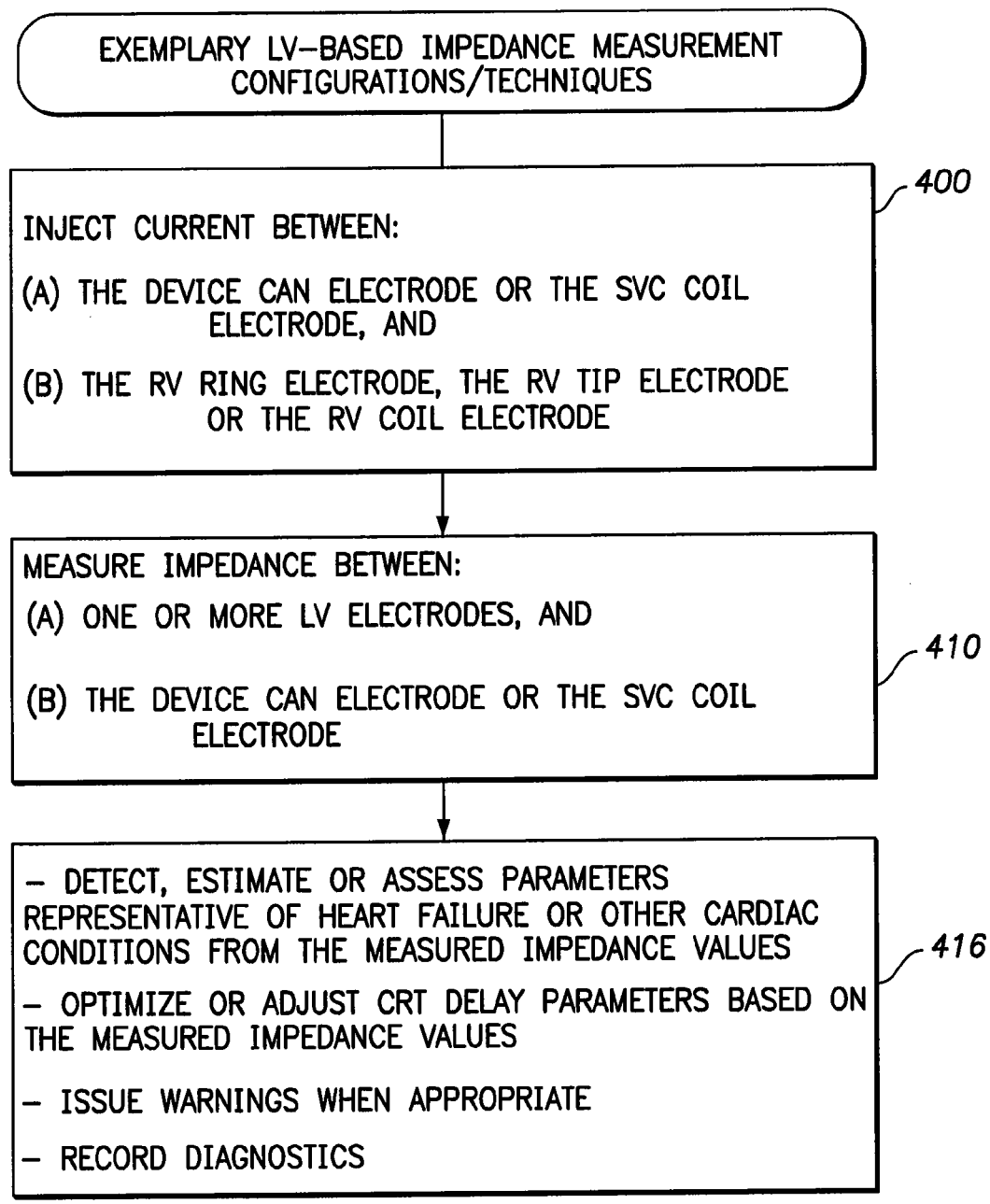
FIG. 6 illustrates some exemplary LV-based impedance measurement techniques for use with the general LV-based technique of FIG. 5.
Figure 7:
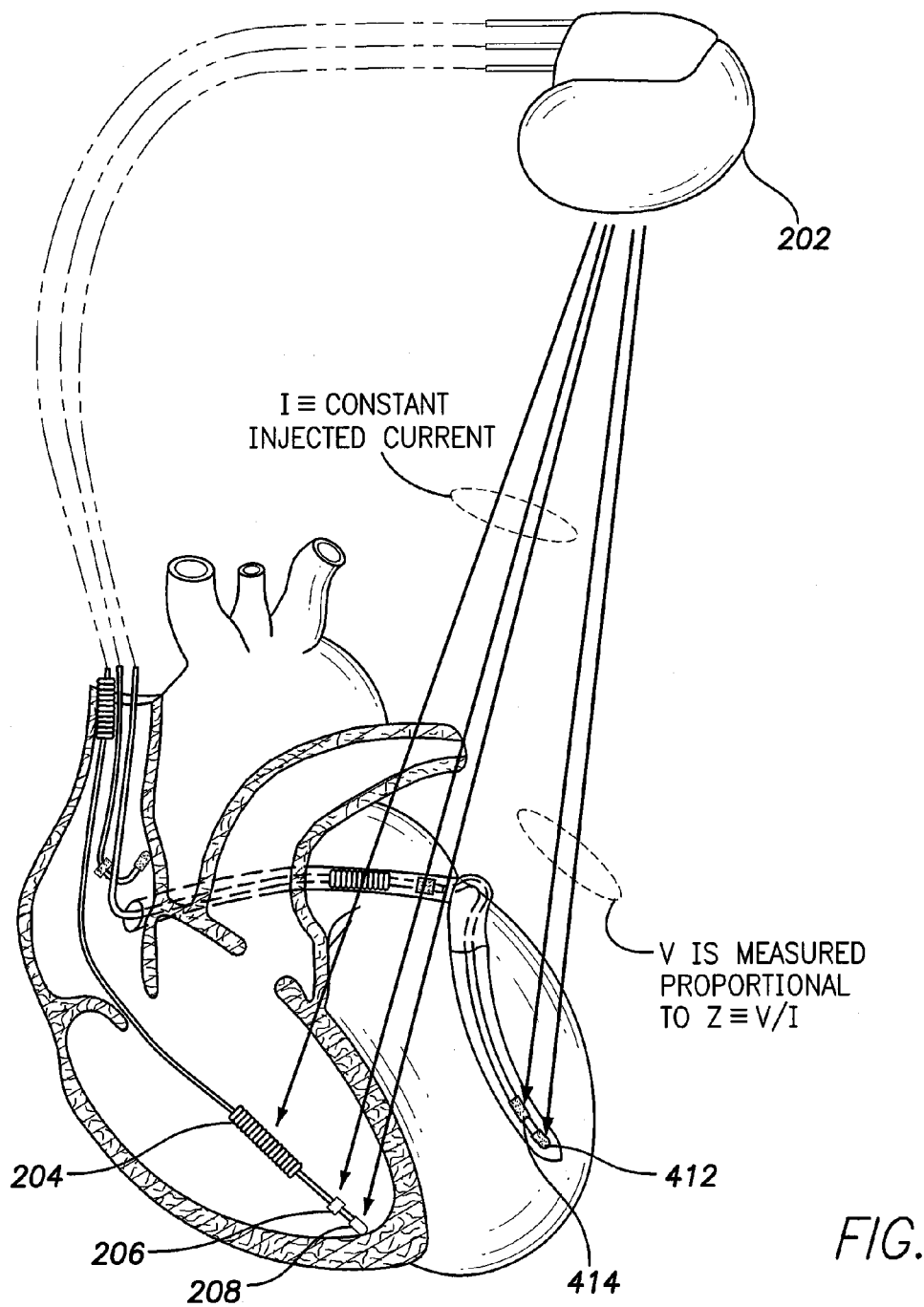
FIG. 7 illustrates vectors for use with the exemplary LV-based techniques of FIG. 3 along with the exemplary lead system.

FIG. 6 summarizes some LV-based configurations. At step 400 (which can be the same as step 300 of FIG. 3), the pacer/ICD injects current between: (A) the device can electrode or the SVC coil electrode and (B) the RV ring electrode, the RV tip electrode or the RV coil electrode. FIG. 7 illustrates these current injection vectors, again showing the device case (or can) electrode 202, the RV coil 204, the RV ring 206 and the RV tip 208, with the injection vectors shown therebetween. Insofar as the injection current is concerned, otherwise conventional techniques may again be used for identifying preferred or optimal values for the magnitude of the injection current. An injection current corresponding to 50 V is appropriate in at least some examples.

At step 410 of FIG. 6, the pacer/ICD measures impedance/voltage between: (A) one or more of the LV electrodes and (B) the device can electrode or the SVC coil electrode. FIG. 7 illustrates the various exemplary impedance measurement vectors between the device case (can) 202 and the LV tip 412 and the LV ring 414, with the impedance/voltage measurement vectors shown therebetween (where the measured voltage is again proportional to Z=V/I, with constant current (I)). In this example, the LV/CS lead is a bipolar lead with tip/ring electrodes. Alternatively, the LV/CS lead might include additional ring electrodes to provide a multi-pole lead. See, for example, the lead system of FIG. 10, discussed below. At step 416 of FIG. 6, the pacer/ICD: detects, estimates or assesses parameters representative of heart failure or other heart conditions from the measured LV-based impedance values; optimizes or adjusts CRT delay parameters based on the measured impedance values; issues warnings when appropriate; and/or records diagnostics. Particular techniques for detecting heart conditions and optimization CRT delays are discussed below for use with LV-based impedance measurements.

Configurations Employing RA-Based and LV-Based Hybrid Configurations

Figure 8:
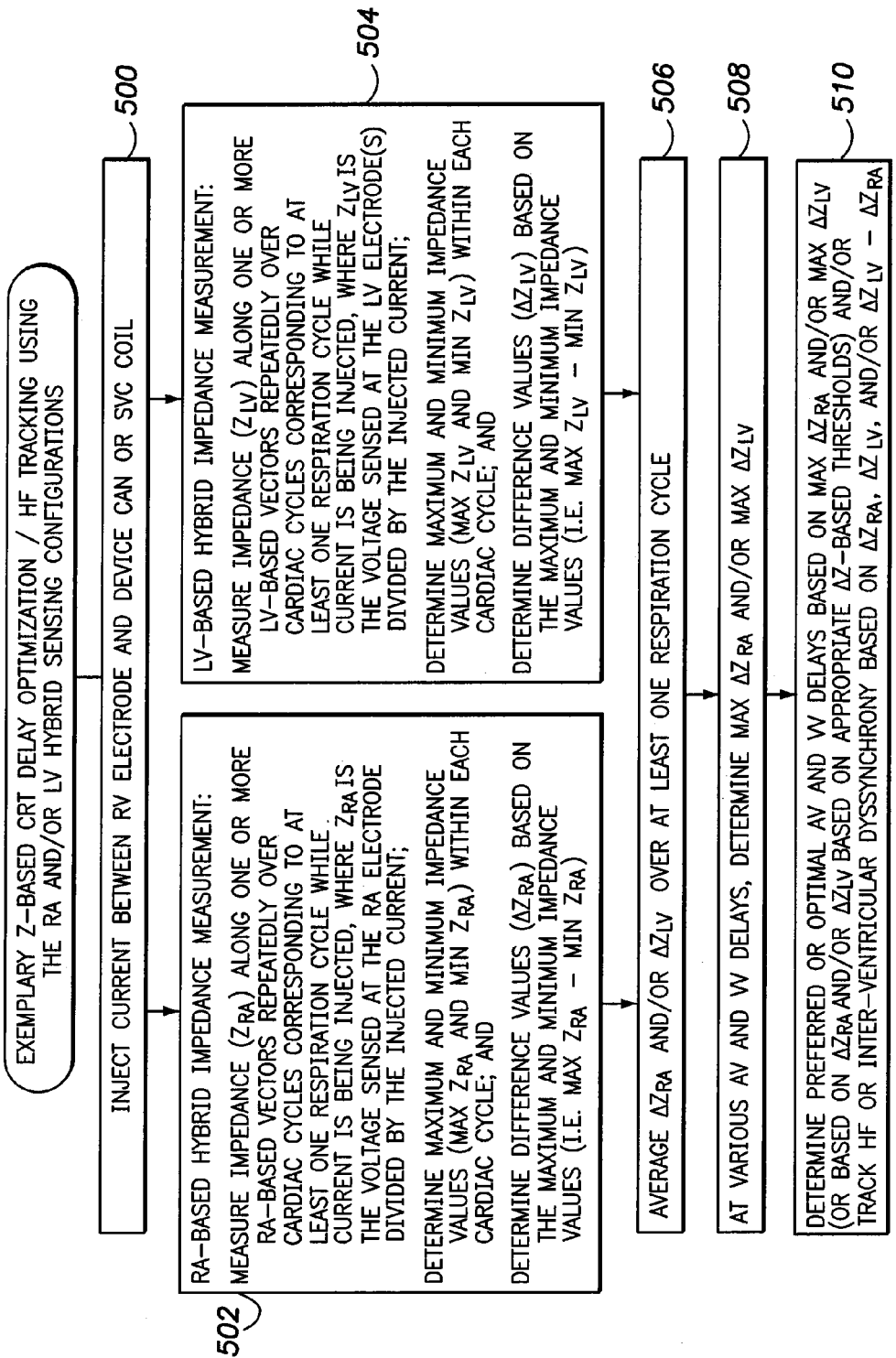
FIG. 8 illustrates exemplary CRT delay optimization techniques and heart failure assessment techniques for use with the RA-based and LV-based configurations/techniques of FIGS. 2-7.

FIG. 8 illustrates exemplary techniques exploiting both RA-based and LV-based hybrid impedance measurement configurations for use in optimizing CRT delays and/or detecting and tracking heart conditions, including conditions related to heart failure. Beginning at step 500, the pacer/ICD injects current between an RV electrode (e.g. RV tip, RV ring or RV coil) and the device can (case) or SVC coil, as already discussed. At step 502, for RA-based impedance measurements, the pacer/ICD measures impedance ($Z_{RA}$) along one or more RA-based vectors repeatedly over cardiac cycles corresponding to at least one respiration cycle while current is being injected, where $Z_{RA}$ is the voltage sensed at the selected RA electrode divided by the injected current (which is substantially constant.) Also at step 502, the device determines maximum and minimum impedance values (max $Z_{RA}$ and min $Z_{RA}$) within each cardiac cycle (i.e. the device assess impedance at end diastolic and end systolic points within the cardiac cycle) and then determines difference values ($\Delta Z_{RA}$) based on the maximum and minimum impedance values by subtracting the min $Z_{RA}$ values (i.e. the end diastolic values) from the corresponding max $Z_{RA}$ values (i.e. the end systolic values).

Concurrently, at step 504, for LV-based impedance measurements, the pacer/ICD measures impedance ($Z_{LV}$) along one or more LV-based vectors repeatedly over cardiac cycles corresponding to at least one respiration cycle while current is being injected, where $Z_{LV}$ is the voltage sensed at the selected LV electrode divided by the injected current. Also at step 504, the device determines maximum and minimum impedance values (max $Z_{LV}$ and min $Z_{LV}$) within each cardiac cycle and then determines difference values ($\Delta Z_{LV}$) based on the maximum and minimum impedance values by subtracting the min $Z_{LV}$ values (i.e. the end diastolic values) from the corresponding max $Z_{LV}$ values (i.e. the end systolic values).

At step 506, the pacer/ICD then averages the $\Delta Z_{RA}$ and/or $\Delta Z_{LV}$ values over at least one respiration cycle to provide a more robust determination of the difference values to allow both left-sided and right-sided heart changes to be advantageously tracked.

At step 508, at various AV and VV delays to be tested, the pacer/ICD determines max $\Delta Z_{RA}$ and/or max $\Delta Z_{LV}$. That is, throughout a range of programmable AV values and a range programmable VV values, the device selects particular AV/VV values and paces the heart using those values. While the heart is being paced, $Z_{RA}$ and $Z_{LV}$ values are measured and the aforementioned $\Delta Z_{RA}$ and/or $\Delta Z_{LV}$ values are determined. The largest value of $\Delta Z_{RA}$ measured during this test is designated as max $\Delta Z_{RA}$ and the AV/VV delay values that achieved that maximum value for $\Delta Z_{RA}$ are identified. The largest value of $\Delta Z_{LV}$ measured during this test is designated as max $\Delta Z_{LV}$ and the AV/VV delay values that achieved that maximum value for $\Delta Z_{LV}$ are identified.

At step 510, the pacer/ICD determines preferred or optimal AV and VV delays based on max $\Delta Z_{RA}$ and/or max $\Delta Z_{LV}$. For example, for implementations where RA-based values are used to determine the AV and VV delays, the device simply uses the AV and VV values identified at step 508 as achieving the maximum value for $\Delta Z_{RA}$. For implementations where LV-based values are used to determine the AV and VV delays, the device simply uses the AV and VV values identified as achieving the maximum value for $\Delta Z_{LV}$. If both max $\Delta Z_{RA}$ and max $\Delta Z_{LV}$ values have been obtained, the device can identify AV and VV values that serve to maximize a combination of max $\Delta Z_{RA}$ and max $\Delta Z_{LV}$ (such as max $\Delta Z_{RA}$ plus max $\Delta Z_{LV}$.) Alternatively, rather than using max $\Delta Z_{RA}$ and/or max $\Delta Z_{LV}$, the device can instead identify preferred or optimal AV and VV delays based on $\Delta Z_{RA}$ and/or $\Delta Z_{LV}$ using appropriate $\Delta Z$-based thresholds. For example, for implementations where RA-based values are used to determine the AV and VV delays, the device can chose a combination of AV and VV values that is sufficient to achieve a $\Delta Z_{RA}$ value that exceeds a predetermined threshold for $\Delta Z_{RA}$ (i.e. $\Delta Z_{RA\_THRESH}$.) For implementations where LV-based values are used to determine the preferred or optimal AV and VV delays, the device can chose a combination of AV and VV values that is sufficient to achieve a $\Delta Z_{LV}$ value that exceeds a predetermined threshold for $\Delta Z_{LV}$ (i.e. $\Delta Z_{LV\_THRESH}$.) If both $\Delta Z_{RA}$ and $\Delta Z_{LV}$ values have been detected, the device can identify AV and VV values sufficient to achieve $\Delta Z_{RA}$ and $\Delta Z_{LV}$ values that exceed a combined threshold. As can be appreciated, a wide variety of specific techniques may be employed to identify the preferred or optimal AV and VV delays. Similar techniques may be used to identify preferred or optimal PV delays.

Insofar as the optimization of AV/PV/VV delays is concerned, the delay values may be adjusted/optimized in conjunction with other optimization techniques. See, for example, the following patents and patent applications that set forth various systems and methods for determining and/or adjusting AV/PV/VV pacing delays: U.S. Pat. No. 7,590,446 of Min et al.; U.S. Published Patent Application 2009/0299423A1; U.S. patent application Ser. No. 11/952,743, filed Dec. 7, 2007, entitled "Systems and Methods for Determining Optimal Atrio-Ventricular Pacing Delays using either Paced or Sensed Atrial Beats"; U.S. Published Patent Application 2010/0145405A1, entitled "Systems and Methods for Controlling Ventricular Pacing in Patients with Long Intra-Atrial Conduction Delays"; U.S. Published Patent Application 2011/0022110A1, of Min et al. entitled "Systems and Methods for Optimizing Ventricular Pacing Delays for use with Multi-Pole Leads"; U.S. Published Patent Application 2011/0022112A1, of Min et al., entitled "Systems and Methods for Determining Ventricular Pacing Sites for use with Multi-Pole Leads"; U.S. Published Patent Application 2011/0098772A1, of Min et al., entitled "Systems and Methods for Determining Optimal Electrode Pairs for use in Biventricular Pacing using Multi-Pole Ventricular Leads"; U.S. patent application Ser. No. 12/957,142, filed Nov. 30, 2010, of Min, entitled "Systems and Methods for Determining Optimal Atrioventricular Pacing Delays based on Cardiomechanical Delays"; and U.S. patent application Ser. No. 12/976,322, filed Dec. 22, 2010, of Min et al., entitled "Systems and Methods for Optimizing AV/VV Pacing Delays using Combined IEGM/Impedance-based Techniques for use with Implantable Medical Devices". See, also, U.S. Pat. No. 7,248,925, to Bruhns et al. entitled "System and Method for Determining Optimal Atrioventricular Delay based on Intrinsic Conduction Delays." At least some of the techniques are implemented within the QuickOpt™ systems of St. Jude Medical.

It should be understood that the "optimal" delays obtained using the techniques described herein are not necessarily absolutely optimal in a given quantifiable or mathematical sense. What constitutes "optimal" depends on the criteria used for judging the resulting performance, which can be subjective in the minds of some clinicians. The pacing delays determined by the techniques described herein represent, at least, "preferred" delays. Clinicians may choose to adjust or alter the selection of the delays for particular patients at their discretion.

The optimized delays may be used in conjunction with CRT techniques in an effort to remodel the heart to improve cardiac function. Briefly, CRT seeks to normalize asynchronous cardiac electrical activation and resultant asynchronous contractions associated with heart failure by delivering synchronized pacing stimulus to both ventricles. The stimulus is synchronized so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis et al., entitled "Multi-Electrode Apparatus and Method for Treatment of Congestive Heart Failure"; U.S. Pat. No. 6,628,988 to Kramer et al., entitled "Apparatus and Method for Reversal of Myocardial Remodeling with Electrical Stimulation"; and U.S. Pat. No. 6,512,952 to Stahmann et al., entitled "Method and Apparatus for Maintaining Synchronized Pacing".

Additionally, at step 510 of FIG. 8, the pacer/ICD detects or tracks heart failure and/or interventricular dyssynchrony based on $\Delta Z_{RA}$, $\Delta Z_{LV}$ and/or $\Delta Z_{LV}$–$\Delta Z_{RA}$. Insofar as heart failure is concerned, in one example a significant and sustained decrease over time in $\Delta Z_{RA}$ and/or $\Delta Z_{LV}$ to below predetermined threshold(s) would be interpreted by the device as an indication of the onset of heart failure (in the absence of confounding factors that might also affect $\Delta Z$ such as changes in activity levels, pacing rates, medications, etc.) A further sustained decrease in $\Delta Z_{RA}$ and/or $\Delta Z_{LV}$ would be interpreted by the device as an indication the progression of heart failure (in the absence of confounding factors.) Additionally or alternatively, the device can estimate stroke volume from $\Delta Z$ (either from $\Delta Z_{RA}$ or $\Delta Z_{LV}$ or both) using techniques described in the Min application incorporated by reference above. Briefly, the device applies a pre-calibrated scaling factor or correlation factor (k) to $\Delta Z$ to yield an estimated value for absolute stroke volume in milliliters (or any other appropriate units) such as by using: SV=k·$\Delta Z$. The device then exploits the estimate of stroke volume to: determine cardiac output; detect and track progression/regression of heart failure; and optimize AV/PV/VV delays to maximize or otherwise improve stroke volume. Cardiac output can be derived from stroke volume based on heart rate. Progression of heart failure may be indicated based on a significant drop in stroke volume/cardiac output over time (in the absence of confounding factors.) Conversely, regression heart failure may be indicated based on significant increase in stroke volume/cardiac output over time (again, in the absence of confounding factors.)

Insofar as interventricular dyssynchrony is concerned, any significant increase in the difference between $\Delta Z_{LV}$ and $\Delta Z_{RA}$ (i.e. $\Delta Z_{LV}$–$\Delta Z_{RA}$) can be interpreted by the device as an indication of increasing dyssynchrony between the left and right ventricles. In one example a significant and sustained increase over time in $\Delta Z_{LV}$–$\Delta Z_{RA}$ to above a predetermined threshold would be interpreted by the device as an indication the onset of interventricular dyssynchrony (in the absence of confounding factors.) A further sustained increase in $\Delta Z_{LV}$–$\Delta Z_{RA}$ would be interpreted by the device as an indication the progression of the dyssynchrony (again, in the absence of confounding factors.) The detection of ventricular dyssynchrony at step 510 can be performed in conjunction with other suitable detection techniques. See, for example, U.S. Published Patent Application 2010/0121397 of Cholette, entitled "System and Method for Evaluating Mechanical Cardiac Dyssynchrony Based on Multiple Impedance Vectors Using an Implantable Medical Device" and U.S. Pat. No. 7,676,264 to Pillai et al., entitled "Systems and Methods for use by an Implantable Medical Device for Evaluating Ventricular Dyssynchrony based on T-wave Morphology."

Configurations Employing Multi-Pole LV-Based Hybrid Configurations

Figure 9:
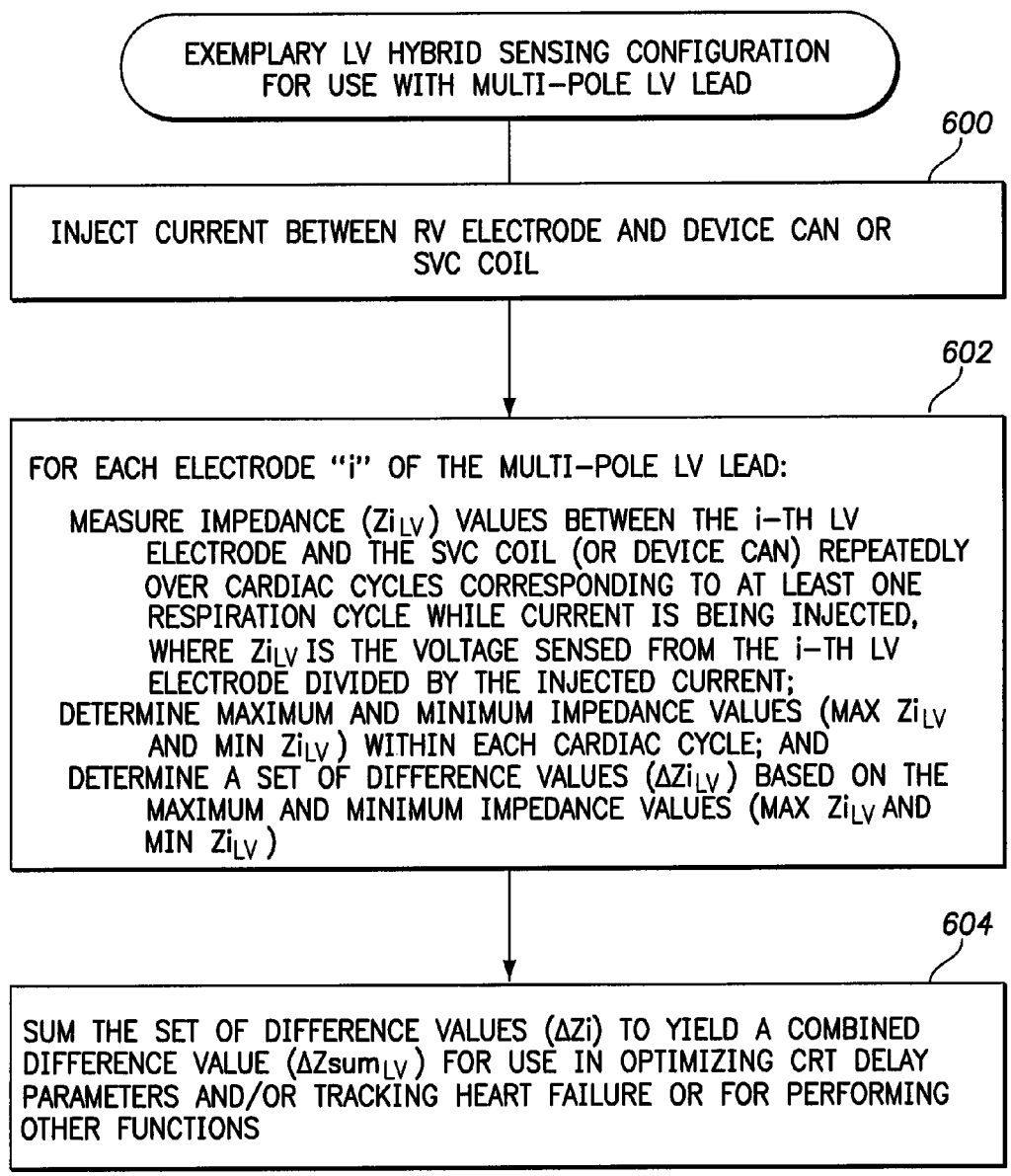
FIG. 9 specifically illustrates hybrid impedance detection techniques employing multi-pole LV leads for use with the various techniques of FIGS. 5-7.

FIG. 9 illustrates exemplary techniques exploiting multi-pole LV-based hybrid impedance measurement configurations for use in optimizing CRT delays and/or detecting and tracking heart conditions, which may be used in conjunction with the RA-based techniques discussed above. Briefly, beginning at step 600, the pacer/ICD injects current between an RV electrode and the device can (case) or SVC coil, as already discussed. At step 602, for each electrode "i" of the multi-pole LV lead, the device measures impedance ($Zi_{LV}$) values between the i-th LV electrode and the SVC coil (or device can) repeatedly over cardiac cycles corresponding to at least one respiration cycle while current is being injected, where $Zi_{LV}$ is the voltage sensed from the i-th LV electrode divided by the injected current. Also at step 602, the device determines maximum and minimum impedance values (max $Zi_{LV}$ and min $Zi_{LV}$) within each cardiac cycle and determines a set of difference values ($\Delta Zi_{LV}$) based on the maximum and minimum impedance values (max $Zi_{LV}$ and min $Zi_{LV}$.) For a quad-pole example using the SVC coil as a reference electrode, the device therefore measures impedance along four vectors (SVC-D1, SVC-M2, SVC-M3 and SVC-P4) throughout each cardiac cycle while current is being applied and then determines four impedance difference values ($\Delta Z_{SVC-D1}$, $\Delta Z_{SVC-M2}$, $\Delta Z_{SVC-M3}$, $\Delta Z_{SVC-P4}$). Data may be collected over multiple cardiac cycle corresponding to at least one respiration cycle and then averaged together to provide a more robust determination of the difference values.

At step 604, the device sums the set of difference values ($\Delta Zi$) to yield a combined difference value ($\Delta Zsum_{LV}$,), i.e. $\Delta Zsum = \Sigma \Delta Zi_{LV}$, for use in optimizing CRT delay parameters and/or tracking heart failure or for performing other functions using techniques already described (i.e. for use in place of the aforementioned $\Delta Z_{LV}$ values.) Alternatively, other procedures or algorithms may be performed to calculate $\Delta Zsum_{LV}$. For example, rather than taking the difference of the individual min and max values and then summing the difference values, the device could instead sum the min values, sum the max values, and then take the difference of the resulting sums to yield a value equivalent to $\Delta Zsum_{LV}$.

Thus various techniques have been described that exploit hybrid impedance measurement configurations, including RA-based and LV-based configurations. In view of the foregoing observations and considerations, when using hybrid configurations it is desirable to select a relatively stable reference electrode, such as the device can (case) or SVC coil for use a current injection reference electrode (in conjunction with an RV electrode) and also as a voltage sensing reference electrode (in conjunction with an RA or LV electrode (or both)). Insofar as the impedance measurement reference electrode is concerned, the less subject it is to patient motion and tissue property changes, the better the performance should be.

Note that to analyze the hybrid configurations, Finite Element Analysis Models were created by using computed tomography (CT) cardiac images. The models included the heart and its four chambers, the SVC, the aorta, and the pulmonary artery (PA) at end of systolic and end of diastolic cardiac cycles. Electrodes of device can, SVC coil, RV ring, RA ring and LV bipolar electrodes were placed inside models for various configurations. The configurations of Large Field Vectors initially studied were SVC-CAN, RV-CAN, SVC-RV. However, the changes in impedance between end diastolic (ED) and end systolic (ES) were less than 2% in these models. For SVC-CAN, the changes in Z were consistent with the finding in animals and in test patients (i.e. about 1 ohm change with direct current impedance (DCZ) of about 55 ohms). Although the signals were small, they were clearly observable and hence acceptable.

Accordingly, additional hybrid configurations were then tested in the models. The additional configurations included:
1. Injecting current RV ring to SVC coil (or Can) while sensing from LV electrodes (i.e. the aforementioned LV-based impedance measurement configuration where the RV ring is specifically used for current injection)
2. Injecting current RV coil to SVC coil (or Can) while sensing from LV electrodes (i.e. the aforementioned LV-based impedance measurement configuration where the RV coil is specifically used for current injection)
3. Injecting current SVC coil to Can while sensing from LV electrodes (i.e. an alternate LV-based impedance measurement configuration where the SVC coil and device can are used for current injection)
4. Injecting current from RV ring to Can while sensing from RA electrode to the Can (i.e. the aforementioned RA-based impedance measurement configuration where the RV ring is specifically used for current injection)
5. Injecting current from RA ring (or tip) to Can while sensing RA ring (or tip) to the Can (i.e. the aforementioned RA-based impedance measurement configuration where the RA ring (or tip) is used for current injection rather than an RV electrode)

Modeling results showed that configuration #1 resulted in a 6% change in Z between ED and ES and hence is preferred. The #2 and #3 configurations showed 2% or less change in Z and hence are deemed less desirable, although still acceptable. Modeling results for configuration #4 showed a 1% change in Z between ED and ES, which is also acceptable. More specifically, the modeling results for Configuration #4 showed Z=40 ohms at EDV with a dZ of 0.43 ohms, i.e. a change in Z of about 1%. It is noted, however, that Configuration #1 might sense more right-sided heart changes and Configuration #2 might sense more left-sided heart changes and hence the selective use Configuration #2 might be advantageous. Also, combining Configurations #1 and #4 can allow both left-sided and right-sided heart changes to be advantageously tracked (FIG. 8.) Modeling results for Configuration #5 showed Z=113.7 ohms at EDV with a dZ of 5.14 ohms, i.e. a change in Z of 4.5%, when current was injected RA ring to can and sensed RA ring to can. With current injected RA ring to can but sensed RA tip to can, even better results were observed with a change in Z of 5.7%. Although no modeling results have yet been generated for the implementation where current is injected RA tip to can and sensed RA ring to can, the same result of 5.7% is likely to be achieved.

Note that the configuration where current is injected between an injection current reference electrode and the RV electrode, with impedance measured between the SVC coil electrode and the device can electrode may be regarded as a sixth configuration (Configuration #6.) This configuration was described above in connection with FIG. 3.

Depending upon the particular implementation, some or all of the steps of the various figures are performed by the implantable device itself. Additionally or alternatively, at least some of the steps can be performed by an external programmer or other external system based on impedance or other data measured within the patient and then transmitted to the external device.

Although primarily described with respect to examples having a pacer/ICD equipped, other implantable medical devices and lead systems may instead be equipped to exploit the techniques described. For the sake of completeness, an exemplary pacer/ICD/CRT device will now be described, which includes components for performing the functions and steps described herein.

Exemplary Pacer/ICD/CRT with Quad-Pole Lead

Figure 10:
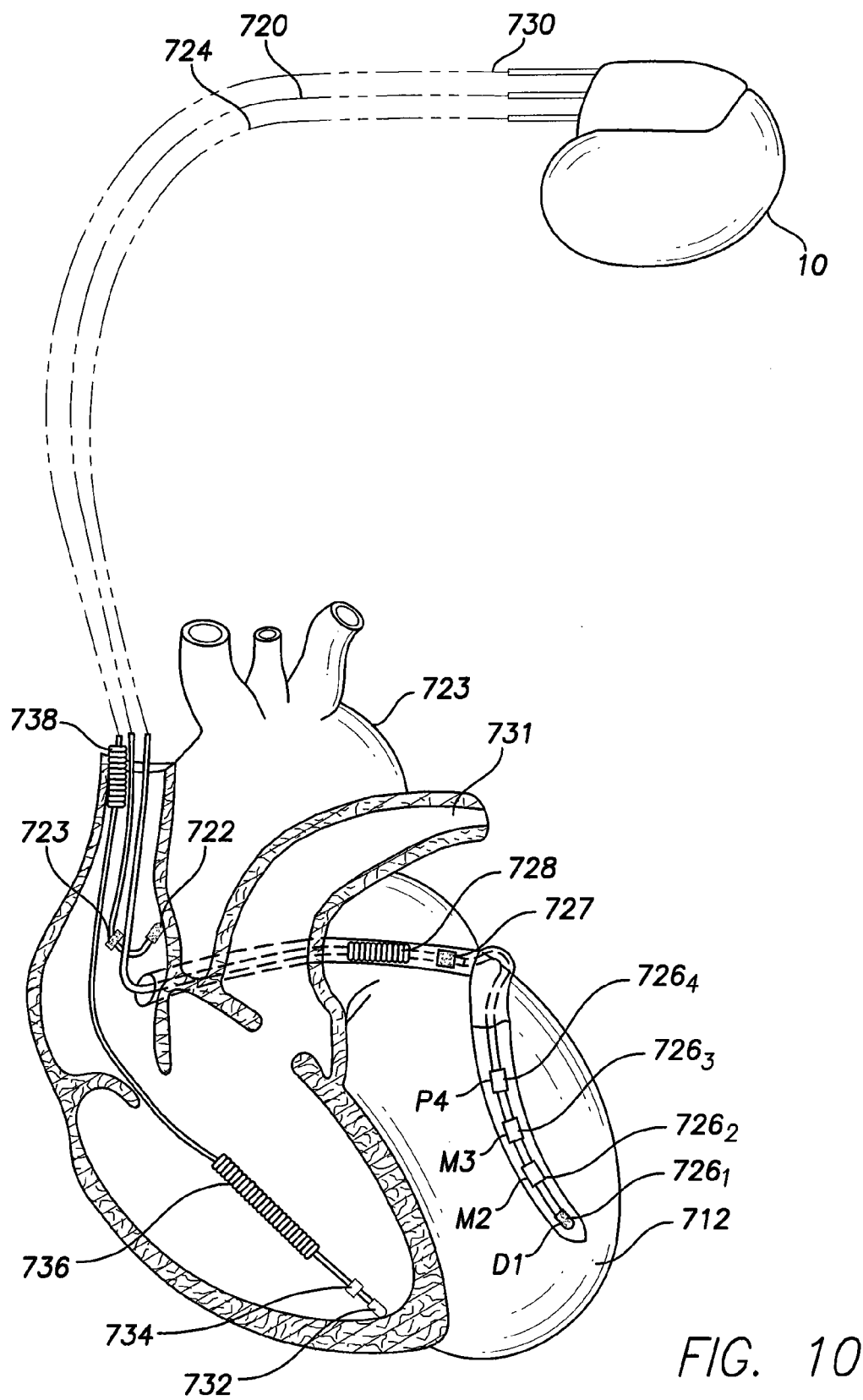
FIG. 10 is a simplified, partly cutaway view, illustrating the device of FIG. 1 along with at set of leads implanted in or on the heart of the patient.
Figure 11:
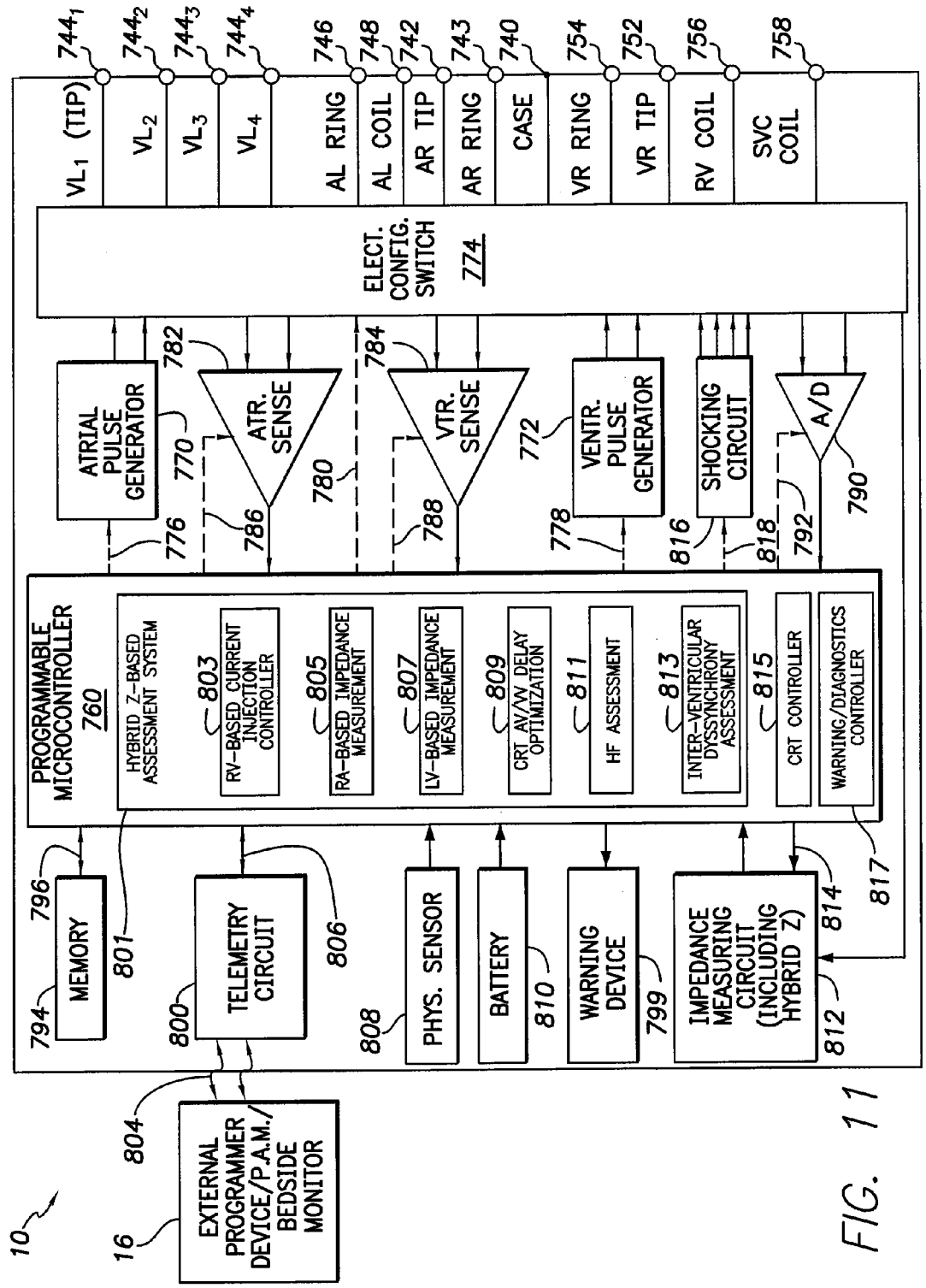
FIG. 11 is a functional block diagram of the pacer/ICD of FIG. 10, illustrating basic circuit elements that provide cardioversion, defibrillation and/or pacing stimulation in the heart and particularly illustrating on-board components for performing the various techniques of FIGS. 2-9.

With reference to FIGS. 10 and 11, a description of an exemplary pacer/ICD/CRT will now be provided. FIG. 10 provides a simplified block diagram of the device, which is a dual-chamber stimulation device capable of treating both fast and slow arrhythmias with stimulation therapy, including cardioversion, defibrillation, and pacing stimulation, and also capable of exploiting hybrid impedance measurement vectors, as discussed above, and controlling functions in response thereto. To provide other atrial chamber pacing stimulation and sensing, device 10 is shown in electrical communication with a heart 712 by way of a left atrial lead 720 having an atrial tip electrode 722 and an atrial ring electrode 723 implanted in the atrial appendage. Device 10 is also in electrical communication with the heart by way of a right ventricular lead 730 having, in this embodiment, a ventricular tip electrode 732, a right ventricular ring electrode 734, a right ventricular (RV) coil electrode 736, and a superior vena cava (SVC) coil electrode 738. Typically, the right ventricular lead 730 is transvenously inserted into the heart so as to place the RV coil electrode 736 in the right ventricular apex, and the SVC coil electrode 738 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, device 10 is coupled to a multi-pole LV lead 724 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 724 is designed to receive atrial and ventricular cardiac signals and to deliver left ventricular pacing therapy using a set of four left ventricular electrodes $726_1$, $726_2$, $726_3$, and $726_4$ (thereby providing a quad-pole lead), left atrial pacing therapy using at least a left atrial ring electrode 727, and shocking therapy using at least a left atrial coil electrode 728 implanted on or near the left atrium. In other examples, more or fewer LV electrodes are provided. Although only three leads are shown in FIG. 10, it should also be understood that additional leads (with one or more pacing, sensing and/or shocking electrodes) might be used and/or additional electrodes might be provided on the leads already shown, such as additional electrodes on the RV lead.

A simplified block diagram of internal components of device 10 is shown in FIG. 10. While a particular device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 740 for device 10, shown schematically in FIG. 11, is often referred to as the "can," "case" or "case electrode" and may be programmably selected to act as the return electrode for all "unipolar" modes. The housing 740 may further be used as a return electrode alone or in combination with one or more of the coil electrodes, 728, 736 and 738, for shocking purposes. The housing 740 further includes a connector (not shown) having a plurality of terminals, 742, 743, $744_1$-$744_4$, 746, 748, 752, 754, 756 and 758 (shown schematically and, for convenience, the names of the electrodes to which they are connected are shown next to the terminals). As such, to achieve right atrial sensing and pacing, the connector includes at least a right atrial tip terminal ($A_R$ TIP) 742 adapted for connection to the atrial tip electrode 722 and a right atrial ring ($A_R$ RING) electrode 743 adapted for connection to right atrial ring electrode 723. To achieve left chamber sensing, pacing and shocking, the connector includes a left ventricular tip terminal ($VL_1$ TIP) $744_1$ and additional LV electrode terminals $744_2$-$744_4$ for the other LV electrodes of the quadra-pole LV lead.

The connector also includes a left atrial ring terminal ($A_L$ RING) 746 and a left atrial shocking terminal ($A_L$ COIL) 748, which are adapted for connection to the left atrial ring electrode 727 and the left atrial coil electrode 728, respectively. To support right chamber sensing, pacing and shocking, the connector further includes a right ventricular tip terminal ($V_R$ TIP) 752, a right ventricular ring terminal ($V_R$ RING) 754, a right ventricular shocking terminal ($V_R$ COIL) 756, and an SVC shocking terminal (SVC COIL) 758, which are adapted for connection to the right ventricular tip electrode 732, right ventricular ring electrode 734, the $V_R$ coil electrode 736, and the SVC coil electrode 738, respectively.

At the core of device 10 is a programmable microcontroller 760, which controls the various modes of stimulation therapy. As is well known in the art, the microcontroller 760 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 760 includes the ability to process or monitor input signals (data) as controlled by a program code stored in a designated block of memory. The details of the design and operation of the microcontroller 760 are not critical to the invention. Rather, any suitable microcontroller 760 may be used that carries out the functions described herein. The use of microprocessor-based control circuits for performing timing and data analysis functions are well known in the art.

As shown in FIG. 11, an atrial pulse generator 770 and a ventricular pulse generator 772 generate pacing stimulation pulses for delivery by the right atrial lead 720, the right ventricular lead 730, and/or the LV lead 724 via an electrode configuration switch 774. It is understood that in order to provide stimulation therapy in each of the four chambers of the heart, the atrial and ventricular pulse generators 770, 772 may include dedicated, independent pulse generators, multiplexed pulse generators or shared pulse generators. The pulse generators 770, 772 are controlled by the microcontroller 760 via appropriate control signals 776, 778 respectively, to trigger or inhibit the stimulation pulses.

The microcontroller 760 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 774 includes a plurality of switches for connecting the desired electrodes to the appropriate I/O circuits, thereby providing complete electrode programmability. Accordingly, the switch 774, in response to a control signal 780 from the microcontroller 760, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 782 and ventricular sensing circuits 784 may also be selectively coupled to the right atrial lead 720, LV lead 724, and the right ventricular lead 730, through the switch 774 for detecting the presence of cardiac activity in each of the four chambers of the heart. Accordingly, the atrial and ventricular sensing circuits 782, 784 may include dedicated sense amplifiers, multiplexed amplifiers or shared amplifiers. The switch 774 determines the "sensing polarity" of the cardiac signal by selectively closing the appropriate switches, as is also known in the art. In this way, the clinician may program the sensing polarity independent of the stimulation polarity. Each sensing circuit 782, 784 preferably employs one or more low power, precision amplifiers with programmable gain and/or automatic gain control, automatic sensitivity control bandpass filtering, and a threshold detection circuit, as known in the art, to selectively sense the cardiac signal of interest. The automatic gain/sensitivity control enables device 10 to deal effectively with the difficult problem of sensing the low amplitude signal characteristics of atrial or ventricular fibrillation. The outputs of the atrial and ventricular sensing circuits 782, 784 are connected to the microcontroller 760 which, in turn, are able to trigger or inhibit the atrial and ventricular pulse generators 770, 772 respectively, in a demand fashion in response to the absence or presence of cardiac activity in the appropriate chambers of the heart.

For arrhythmia detection, device 10 utilizes the atrial and ventricular sensing circuits 782, 784, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 760 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 790. The data acquisition system 790 is configured to acquire intracardiac electrogram signals, convert the raw analog data into a digital signal, and store the digital signals for later processing and/or telemetric transmission to an external device 802. The data acquisition system 790 is coupled to the right atrial lead 720, the LV lead 724, and the right ventricular lead 730 through the switch 774 to sample cardiac signals across any pair of desired electrodes. The microcontroller 760 is further coupled to a memory 794 by a suitable data/address bus 796, wherein the programmable operating parameters used by the microcontroller 760 are stored and modified, as required, in order to customize the operation of device 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable device 10 may be non-invasively programmed through the memory 794 through a telemetry circuit 800 in telemetric communication with the external device 802, such as a programmer, transtelephonic transceiver or a diagnostic system analyzer. The telemetry circuit 800 is activated by the microcontroller by a control signal 806. The telemetry circuit 800 advantageously allows intracardiac electrograms and status information relating to the operation of device 10 (as contained in the microcontroller 760 or memory 794) to be sent to the external device 802 through an established communication link 804. Device 10 further includes an accelerometer or other physiologic sensor 808, commonly referred to as a "rate-responsive" sensor because it is typically used to adjust pacing stimulation rate according to the exercise state of the patient. However, the physiological sensor 808 may further be used to detect changes in cardiac output, changes in the physiological condition of the heart, or diurnal changes in activity (e.g., detecting sleep and wake states) and to detect arousal from sleep. Accordingly, the microcontroller 760 responds by adjusting the various pacing parameters (such as rate, AV delay, VV delay, etc.) at which the atrial and ventricular pulse generators 770, 772 generate stimulation pulses. While shown as being included within device 10, it is to be understood that the physiologic sensor 808 may also be external to device 10, yet still be implanted within or carried by the patient. A common type of rate responsive sensor is an activity sensor incorporating an accelerometer or a piezoelectric crystal, which is mounted within the housing 740 of device 10. Other types of physiologic sensors are also known, for example, sensors that sense the oxygen content of blood, respiration rate and/or minute ventilation, pH of blood, ventricular gradient, etc. Still further, the sensor may be equipped to detect left atrial pressure (LAP), left ventricular pressure (LVP), right ventricular pressure (RVP), photoplethysmography (PPG) or S1 heart sounds. It should be understood that multiple separate sensors can be provided and, depending upon the parameter to be detected, at least some of the sensor might be positioned external to the device housing.

The device additionally includes a battery 810, which provides operating power to all of the circuits shown in FIG. 11. The battery 810 may vary depending on the capabilities of device 10. If the system only provides low voltage therapy, a lithium iodine or lithium copper fluoride cell typically may be utilized. For device 10, which employs shocking therapy, the battery 810 should be capable of operating at low current drains for long periods, and then be capable of providing high-current pulses (for capacitor charging) when the patient requires a shock pulse. The battery 810 should also have a predictable discharge characteristic so that elective replacement time can be detected. Accordingly, appropriate batteries are employed.

As further shown in FIG. 11, device 10 is shown as having an impedance measuring circuit 812, which is enabled by the microcontroller 760 via a control signal 814. Uses for an impedance measuring circuit include, but are not limited to, detecting cardiogenic impedance for the purposes of detecting the onset of isovolumic ventricular contraction; lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; detecting the opening of heart valves; assessing aspects of cardiac function as discussed above, etc. The impedance measuring circuit 812 is advantageously coupled to the switch 874 so that any desired electrode may be used, including the aforementioned hybrid configurations.

In the case where device 10 is intended to operate as an ICD device, it detects the occurrence of an arrhythmia, and automatically applies an appropriate electrical shock therapy to the heart aimed at terminating the detected arrhythmia. To this end, the microcontroller 760 further controls a shocking circuit 816 by way of a control signal 818. The shocking circuit 816 generates shocking pulses of low (up to 0.5 joules), moderate (0.5-10 joules) or high energy (11 to 40 joules or more), as controlled by the microcontroller 760. Such shocking pulses are applied to the heart of the patient through at least two shocking electrodes, and as shown in this embodiment, selected from the left atrial coil electrode 728, the RV coil electrode 736, and/or the SVC coil electrode 14. The housing 740 may act as an active electrode in combination with the RV electrode 736, or as part of a split electrical vector using the SVC coil electrode 14 or the left atrial coil electrode 728 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 760 is capable of controlling the synchronous or asynchronous delivery of the shocking pulses.

The microcontroller includes an on-board hybrid Z-based assessment system 801 operative to perform or control all or some of the assessment techniques described above, particularly the aforementioned RA-based and LV-based assessment techniques. System 801 includes an RV-based current injection controller 803 operative to control the injection of current between the device can (or SVC coil or other suitable current injection reference electrode) and the RV ring (or other electrode in the RV.) An RA-based impedance measurement controller 805 is operative to measure values representative of impedance along sensing vectors between the device can and one more electrodes in or near the RA while the current is being injected. An LV-based impedance measurement controller 807 is operative to measure values representative of impedance along sensing vectors between the device can and one more electrodes on or near the LV while the current is being injected.

A CRT AV/VV delay optimization controller 809 is operative to determine preferred or optimal AV/VV delay values based on the measured impedance values. A heart failure assessment system 811 is operative to detect and track heart failure based on the measured impedance values (or parameters derived therefrom.) An interventricular dyssynchrony assessment system 813 is operative to detect and track interventricular dyssynchrony based on the measured impedance values (or parameters derived therefrom.) A CRT controller 815 controls the delivery of CRT. A warning/diagnostics controller 817 generating warnings and records suitable diagnostics data. An internal warning device 799 may be provided for generating perceptible warning signals to the patient via vibration, voltage or other methods. Diagnostic data may be recorded in memory 794.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

As noted, at least some of the techniques described herein can be performed by (or under the control of) an external device. For the sake of completeness, an exemplary device programmer will now be described, which includes components for controlling at least some of the functions and steps already described.

Exemplary External Programmer

Figure 12:
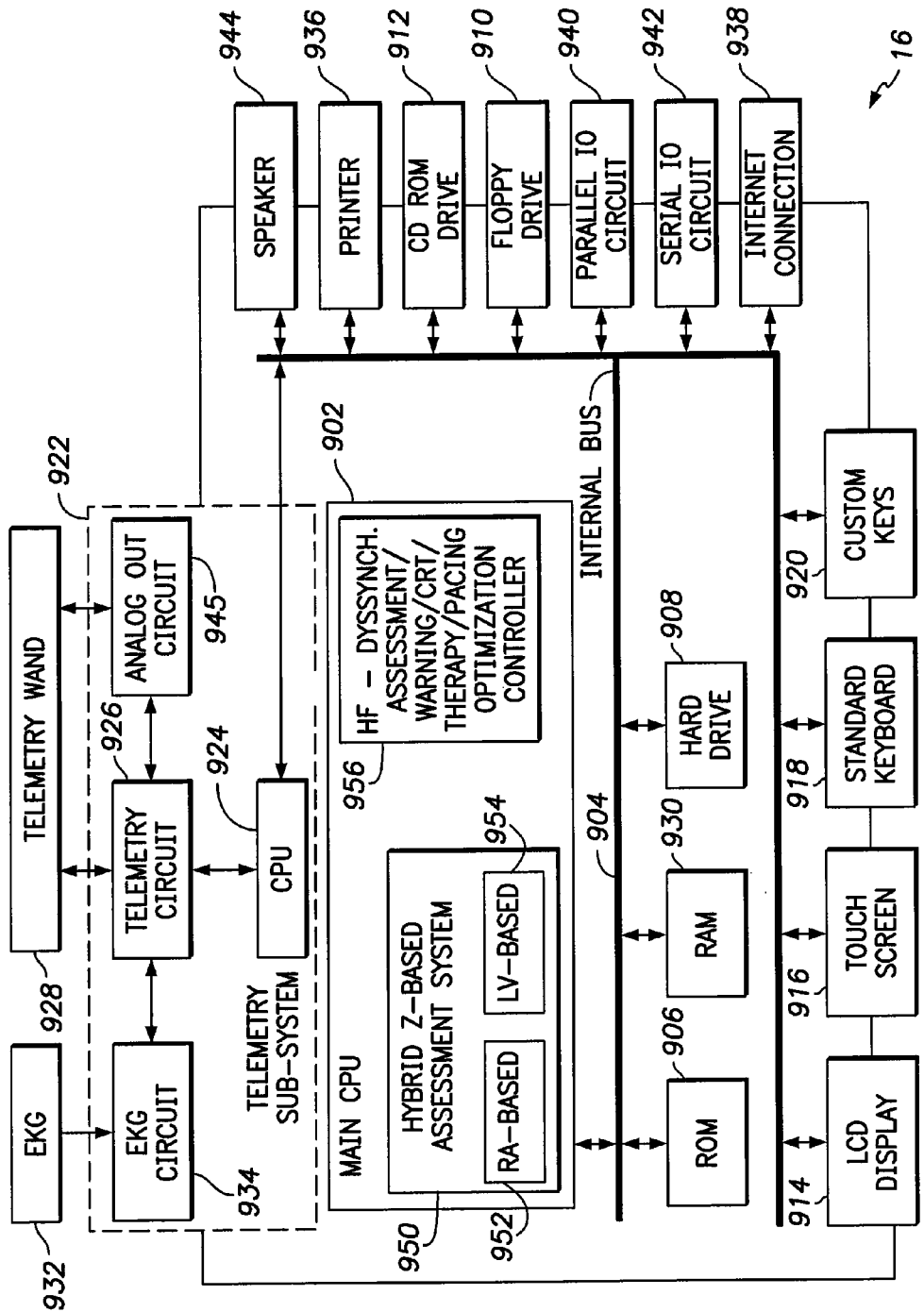
FIG. 12 is a functional block diagram illustrating components of the external device programmer of FIG. 1 and particularly illustrating programmer-based components for controlling or performing the techniques of FIGS. 2-9.

FIG. 12 illustrates pertinent components of an external programmer 16 for use in programming the device of FIG. 11 and for performing or controlling the above-described assessment techniques. For the sake of completeness, other device programming functions are also described herein. Generally, the programmer permits a physician, clinician or other user to program the operation of the implanted device and to retrieve and display information received from the implanted device such as intracardiac electrogram (IEGM) data and device diagnostic data. Additionally, the external programmer can be optionally equipped to receive and display electrocardiogram (ECG) data from separate external surface ECG leads that may be attached to the patient. Depending upon the specific programming of the external programmer, programmer 16 may also be capable of processing and analyzing data received from the implanted device and from the ECG leads to, for example, render preliminary diagnosis as to medical conditions of the patient or to the operations of the implanted device.

Now, considering the components of programmer 16, operations of the programmer are controlled by a CPU 902, which may be a generally programmable microprocessor or microcontroller or may be a dedicated processing device such as an ASIC or the like. Software instructions to be performed by the CPU are accessed via an internal bus 904 from a read only memory (ROM) 906 and random access memory 930. Additional software may be accessed from a hard drive 908, floppy drive 910, and CD ROM drive 912, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 914 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 916 overlaid on the LCD display or through a standard keyboard 918 supplemented by additional custom keys 920, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 16 to retrieve data stored within any implanted devices and to also retrieve ECG data from ECG leads, if any, coupled to the patient. To this end, CPU 902 transmits appropriate signals to a telemetry subsystem 922, which provides components for directly interfacing with the implanted devices, and the ECG leads. Telemetry subsystem 922 includes its own separate CPU 924 for coordinating the operations of the telemetry subsystem. Main CPU 902 of programmer communicates with telemetry subsystem CPU 924 via internal bus 904. Telemetry subsystem additionally includes a telemetry circuit 926 connected to telemetry wand 928, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an ECG circuit 934 for receiving surface ECG signals from a surface ECG system 932. In other implementations, the ECG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the device also includes the data stored within the recalibration database of the device (assuming the device is equipped to store that data.) Data retrieved from the implanted devices is stored by external programmer 16 either within a random access memory (RAM) 930, hard drive 908 or within a floppy diskette placed within floppy drive 910. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 16, the implanted devices may be further controlled to transmit additional data in real time as it is detected by the implanted devices, such as additional IEGM data, lead impedance data, and the like. Additionally, or in the alternative, telemetry subsystem 922 receives ECG signals from ECG leads 932 via an ECG processing circuit 934. As with data retrieved from the implanted device itself, signals received from the ECG leads are stored within one or more of the storage devices of the external programmer. Typically, ECG leads output analog electrical signals representative of the ECG. Accordingly, ECG circuit 934 includes analog to digital conversion circuitry for converting the signals to digital data appropriate for further processing within the programmer. Depending upon the implementation, the ECG circuit may be configured to convert the analog signals into event record data for ease of processing along with the event record data retrieved from the implanted device. Typically, signals received from the ECG leads are received and processed in real time.

Thus, the programmer receives data both from the implanted devices and from optional external ECG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 902, the programming commands are converted to specific programmable parameters for transmission to the implanted devices via telemetry wand 928 to thereby reprogram the implanted devices. Prior to reprogramming specific parameters, the physician may control the external programmer to display any or all of the data retrieved from the implanted devices or from the ECG leads, including displays of ECGs, IEGMs, and statistical patient information. Any or all of the information displayed by programmer may also be printed using a printer 936.

Additionally, CPU 902 also includes a programmer-based hybrid Z-based assessment system 950 operative to perform all or some of the functions of corresponding on-board system 801, discussed above, based on data transmitted to/from the implanted device such as the aforementioned hybrid impedance parameters. System 950 includes an RA-based system 952 and an LV-based system operative to process RA-based and LV-based impedance measurements, respectively. The microcontroller also includes a programmer-based HF-dyssynchrony assessment/warning/CRT/therapy/pacing optimization controller 956 operative to perform or control all or some of the functions described above in response to the hybrid impedance measurements, such as detecting and tracking heart failure, generating warnings, controlling CRT, optimizing pacing delay parameters, etc.

Depending upon the implementation, the various components of the CPU may be implemented as separate software modules or the modules may be combined to permit a single module to perform multiple functions. In addition, although shown as being components of the CPU, some or all of these components may be implemented separately using ASICs or the like.

Programmer/monitor 16 also includes an internet connection 938 to permit direct transmission of data to other programmers via the public switched telephone network (PSTN) or other interconnection line, such as a T1 line or fiber optic cable or wireless connection (WiFi). Depending upon the implementation, the internet connection may be connected directly to internal bus 904 may be connected to the internal bus via either a parallel port 940 or a serial port 942. Other peripheral devices may be connected to the external programmer via parallel port 940 or a serial port 942 as well. Although one of each is shown, a plurality of input output (I/O) ports might be provided, including USB ports, etc. A speaker 944 is included for providing audible tones to the user, such as a warning beep in the event improper input is provided by the physician. Telemetry subsystem 922 additionally includes an analog output circuit 945 for controlling the transmission of analog output signals, such as IEGM signals output to an ECG machine or chart recorder.

With the programmer configured as shown, a clinician or other user operating the external programmer is capable of retrieving, processing and displaying a wide range of information received from the implanted device and to reprogram the implanted device if needed. The descriptions provided herein with respect to FIG. 12 are intended merely to provide an overview of the operation of programmer and are not intended to describe in detail every feature of the hardware and software of the programmer and is not intended to provide an exhaustive list of the functions performed by the programmer.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable medical device for implant within a patient having a lead system including a right ventricular (RV) lead and a right atrial (RA) lead, the method comprising:
    injecting current between an injection current reference electrode and an RV electrode of the RV lead;
    measuring values representative of impedance along a vector between a voltage sensing reference electrode and an RA electrode of the RA lead; and
    controlling at least one device function based on the values representative of impedance;
    wherein measuring values representative of impedance using the RA electrode includes:
    measuring impedance ($Z_{RA}$) values over cardiac cycles corresponding to at least one respiration cycle while the current is being infected;
    determining maximum and minimum impedance values (max $Z_{RA}$ and min $Z_{RA}$) with each cardiac cycle; and
    determining difference values ($\Delta Z_{RA}$) based on the maximum and minimum impedance values (max $Z_{RA}$ min $Z_{RA}$); and further including:
    determining AV and VV pacing delays that achieve a maximum value for $AZ_{RA}$ from among a set of AV and VV delay values.

2. The method of claim 1 wherein the injection current reference electrode is a relatively large electrode compared to the RV electrode.

3. The method of claim 2 wherein the injection current reference electrode is a device can electrode.

4. The method of claim 2 wherein the injection current reference electrode is a superior vena cava (SVC) coil electrode.

5. The method of claim 2 wherein the RV electrode comprises at least one of an RV tip electrode, an RV ring electrode, and an RV coil electrode.

6. The method of claim 1 wherein the voltage sensing reference electrode is relatively large compared to the RA electrode.

7. The method of claim 6 wherein the voltage sensing reference electrode is one or more of a device can electrode and an SVC coil electrode.

8. The method of claim 6 wherein the RA electrode comprises at least one of an RA tip electrode and an RA ring electrode.

9. The method of claim 1 further including determining AV and VV pacing delays based on $\Delta Z_{RA}$ using a predetermined threshold.

10. The method of claim 1 further including assessing a heart condition from the difference values ($\Delta Z_{RA}$).

11. The method of claim 10 wherein the heart condition includes one or more of heart failure and interventricular dyssynchrony.

12. The method of claim 1 wherein the lead system additionally includes a left ventricular (LV) lead and wherein the method further comprises:
    measuring additional values representative of impedance along a sensing vector between the voltage sensing reference electrode and an electrode implanted on the LV.

13. The method of claim 12 wherein measuring the additional values representative of impedance using the electrode implanted on the LV includes:

measuring impedance ($Z_{LV}$) values over cardiac cycles corresponding to at least one respiration cycle while the current is being injected;

determining maximum and minimum impedance values (max $Z_{LV}$ and min $Z_{LV}$) with each cardiac cycle; and determining difference values ($\Delta Z_{LV}$) based on the maximum and minimum impedance values (max $Z_{LV}$ and min $Z_{LV}$).

14. The method of claim 13 further including determining AV and VV pacing delays from a combination of the $\Delta Z_{RA}$ and $\Delta Z_{RA}$ difference values.

15. The method of claim 13 further including assessing a heart condition from a combination of the $\Delta Z_{RA}$ and $\Delta Z_{RA}$ difference values.

16. The method of claim 12 wherein the LV lead is a multi-pole LV lead and wherein the method further comprises:

measuring additional values representative of impedance along a plurality of different sensing vectors between the voltage sensing reference electrode and a plurality of LV electrodes.

17. The method of claim 16 wherein multi-pole LV lead includes a tip electrode and a set of ring electrodes.

18. The method of claim 17 wherein the multi-pole LV lead is quad-pole lead comprising the tip electrode and three ring electrodes.

19. The method of claim 1 wherein the lead system includes an SVC coil electrode and wherein the method further comprises:

measuring additional values representative of impedance along a sensing vector between a device can electrode and the SVC coil electrode.

20. The method of claim 1 wherein controlling at least one device function includes controlling the delivery of pacing using AV and VV pacing delay values set based on the values representative of impedance.

21. The method of claim 1 wherein controlling at least one device function includes generating warning signals based on an assessment of a heart condition determined from the values representative of impedance.

22. The method of claim 1 wherein all of the steps are performed by the implantable medical device.

23. The method of claim 1 wherein at least some of the steps are performed by an external device based on signals received from the implantable medical device.

24. The method of claim 1 wherein the values representative of impedance include one or more of impedance, admittance, conductance and immittance.

25. A method for use with an implantable medical device for implant within a patient having a lead system including a right ventricular (RV) lead and a right atrial (RA) lead, the method comprising:

injecting current between an injection current reference electrode and an RV electrode of the RV lead;

measuring values representative of impedance along a vector between a voltage sensing reference electrode and an RA electrode of the RA lead; and controlling at least one device function based on the values representative of impedance;

wherein measuring values representative of impedance using the RA electrode includes:

measuring impedance ($Z_{RA}$) values over cardiac cycles corresponding to at least one respiration cycle while the current is being injected;

determining maximum and minimum impedance values max $Z_{RA}$ and min $Z_{RA}$) with each cardiac cycle; and determining difference values ($\Delta Z_{RA}$) based on the maximum and minimum impedance values (max $Z_{RA}$ and $Z_{RA}$); and further including:

wherein the lead system additionally includes a left ventricular (LV) lead and wherein the method further comprises:

measuring additional values representative of impedance along a sensing vector between the voltage sensing reference electrode and an electrode implanted on the LV;

wherein the LV lead is a multi-pole LV lead and wherein the method further comprises:

measuring additional values representative of impedance along a plurality of different sensing vectors between the voltage sensing reference electrode and a plurality of LV electrodes;

wherein measuring the additional values representative of impedance using the plurality of LV electrodes includes:

for each electrode "i" of the multi-pole LV lead, measuring impedance ($Zi_{LV}$) values between the i-th LV electrode and the voltage sensing reference electrode repeatedly over cardiac cycles corresponding to at least one respiration cycle while current is being injected where $Zi_{LV}$ is the voltage sensed from the i-th LV electrode divided by the injected current;

determining maximum and minimum impedance values (max $Zi_{LV}$ and min $Zi_{LV}$) within each heartbeat; and determining a set of difference values ($\Delta Zi_{LV}$) based on the maximum and minimum impedance values (max $Zi_{LV}$ and min $Zi_{LV}$).

* * * * *